United States Patent
Kaneko et al.

(10) Patent No.: US 8,735,529 B2
(45) Date of Patent: May 27, 2014

(54) CLATHRATE COMPOUND, CURING CATALYST, COMPOSITION FOR FORMING CURED RESIN, AND CURED RESIN

(75) Inventors: Masami Kaneko, Ichihara (JP); Natsuki Amanokura, Ichihara (JP)

(73) Assignee: Nippon Soda Co., Ltd., Tokyo (JP)

( * ) Notice: Subject to any disclaimer, the term of this patent is extended or adjusted under 35 U.S.C. 154(b) by 216 days.

(21) Appl. No.: 13/331,772

(22) Filed: Dec. 20, 2011

(65) Prior Publication Data

US 2012/0088920 A1    Apr. 12, 2012

Related U.S. Application Data

(63) Continuation-in-part of application No. 12/448,248, filed as application No. PCT/JP2006/325472 on Dec. 21, 2006, now abandoned.

(51) Int. Cl.
C07C 63/24 (2006.01)
C08G 59/68 (2006.01)
C08L 63/00 (2006.01)

(52) U.S. Cl.
USPC ............................ 528/113; 525/533; 562/480

(58) Field of Classification Search
None
See application file for complete search history.

(56) References Cited

U.S. PATENT DOCUMENTS

| | | | |
|---|---|---|---|
| 3,746,686 A | 7/1973 | Marshall et al. | |
| 3,847,612 A | 11/1974 | Winslow | |
| 4,244,989 A | 1/1981 | Noomen | |
| 4,420,605 A | 12/1983 | Kaufman | |
| 5,153,239 A | 10/1992 | Kitagawa et al. | |
| 6,727,325 B1 | 4/2004 | Suzuki et al. | |
| 2003/0008991 A1 | 1/2003 | Holmes et al. | |
| 2003/0054146 A1 | 3/2003 | Kim et al. | |
| 2010/0016475 A1 | 1/2010 | Doering et al. | |
| 2010/0022744 A1 | 1/2010 | Kaneko et al. | |
| 2010/0179250 A1* | 7/2010 | Ono et al. ..................... | 523/455 |
| 2012/0004349 A1 | 1/2012 | Kaneko et al. | |
| 2012/0004377 A1* | 1/2012 | Kaneko et al. ................ | 525/533 |
| 2012/0196991 A1 | 8/2012 | Ono et al. | |
| 2013/0059942 A1 | 3/2013 | Ono et al. | |
| 2013/0158231 A1 | 6/2013 | Kamegaya et al. | |

FOREIGN PATENT DOCUMENTS

| | | | |
|---|---|---|---|
| EP | 62-1256 A1 * | 10/1994 | |
| EP | 0 949 286 A1 | 10/1999 | |
| JP | A-49-032999 | 3/1974 | |
| JP | 56-100748 A * | 8/1981 | |
| JP | A-56-100748 | 8/1981 | |
| JP | A-57-135870 | 8/1982 | |
| JP | A-58-076420 | 5/1983 | |
| JP | A-60-252620 | 12/1985 | |
| JP | A-01-096278 | 4/1989 | |
| JP | B2-04-002638 | 1/1992 | |
| JP | A-4-266922 | 9/1992 | |
| JP | A-05-194711 | 8/1993 | |
| JP | A-06-100662 | 4/1994 | |
| JP | A-08-151372 | 6/1996 | |
| JP | A-09-143250 | 6/1997 | |
| JP | A-10-511718 | 11/1998 | |
| JP | A-10-316639 | 12/1998 | |
| JP | A-10-324826 | 12/1998 | |
| JP | A-11-071449 | 3/1999 | |
| JP | A-11-158253 | 6/1999 | |
| JP | A-2000-248053 | 9/2000 | |
| JP | A 2001-172225 | 6/2001 | |
| JP | A-2002-20714 | 1/2002 | |

(Continued)

OTHER PUBLICATIONS

Lin et al., "Aromatic Polyoxyalkylene Amidoamines as Curatives for Epoxy Resins-Derivatives from t-Butyl Isophthalic Acid," Journal of Polymer Research, vol. 3, No. 2, Apr. 1996, pp. 97-104.*
Luo et al., "A Novel Bilayer Cobalt(II)—Organic Framework with Nanoscale Channels Accomodating Large Organic Molecules," Inorganic Chemistry, vol. 42, No. 15, 2003, pp. 4486-4488.*
Feb. 1, 2013 Office Action issued in U.S. Appl. No. 12/733,462.
Sep. 7, 2012 Office Action cited in U.S. Appl. No. 12/733,462, filed Mar. 3, 2010.
Jun. 15, 2010 International Search Report issued in International Application No. PCT/JP2010/001663 with English-language translation.

(Continued)

Primary Examiner — Robert Sellers
(74) Attorney, Agent, or Firm — Oliff PLC

(57) ABSTRACT

A curing catalyst (clathrate compound) for which the curing reaction is suppressed at low temperatures, allowing an improvement in the one-pot stability, but which can effectively cure a resin upon heat treatment. The clathrate compound includes at least an isophthalic acid compound represented by Formula (I), where $R_1$ represents a C1 to C6 alkyl group, a C1 to C6 alkoxy group, a nitro group, or a hydroxyl group, and an imidazole compound represented by a Formula (II) where $R_2$ represents a hydrogen atom, a C1 to C10 alkyl group, a phenyl group, a benzyl group, or a cyanoethyl group, and $R_3$ to $R_5$ each independently represents a hydrogen atom, a nitro group, or a halogen atom, or a C1 to C20 alkyl group, phenyl group, benzyl group, or C1 to C20 acyl group that may have a substituent.

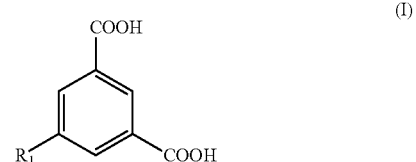

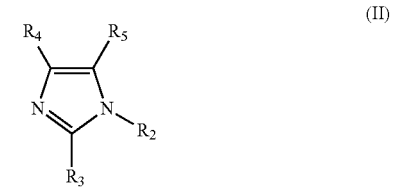

12 Claims, 22 Drawing Sheets

(56) References Cited

FOREIGN PATENT DOCUMENTS

| JP | A-2002-047337 | 2/2002 |
|---|---|---|
| JP | A-2004-503632 | 2/2004 |
| JP | A-2004-210677 | 7/2004 |
| JP | A-2004-300041 | 10/2004 |
| JP | A 2004-300256 | 10/2004 |
| JP | A 2004-307545 | 11/2004 |
| JP | A-2006-016542 | 1/2006 |
| JP | A 2006-206731 | 8/2006 |
| JP | A-2007-039449 | 2/2007 |
| TW | 200909467 A | 3/2009 |
| WO | WO 96/20253 A1 | 7/1996 |
| WO | WO 2006/128542 A1 | 12/2006 |
| WO | WO 2008/075427 A1 | 6/2008 |
| WO | WO 2008/143314 A1 | 11/2008 |
| WO | WO 2009/037862 A1 | 3/2009 |

OTHER PUBLICATIONS

Jun. 14, 2013 Office Action issued in U.S. Appl. No. 12/733,462.
May 20, 2013 Restriction Requirement issued in U.S. Appl. No. 13/138,568.
Jul. 18, 2012 Supplementary European Search Report issued in European Application No. 08832343.1.
Dec. 16, 2008 International Search Report issued in corresponding International Application No. PCT/JP2008/002603.
Apr. 7, 2010 International Preliminary Report on Patentability and Written Opinion issued in corresponding PCT/JP2008/002603.
Oct. 6, 2010 Hungarian Patent Office Search Report issued in corresponding Singapore Application No. 2010016608.
Luo et al, "A Novel Bilayer Cobalt(II)-Organic Framework with Nanoscale Channels Accommodating Large Organic Molecules," *Inorganic Chemistry*, vol. 42, pp. 4486-4488, 2003.
Chen et al., "Synthesis, structures of cobalt/copper complexes and magnetic property of copper complex with the mixed ligands 5-nitro-1,3-benzenedicarboxylic acid and imidazole," *Inorganic Chemistry Communications*, 2006, vol. 9, pp. 300-303.
Lin et al., "Aromatic Polyoxyalkylene Amidoamines as Curatives for Epoxy Resins-Derivatives from t-Butyl Isophthalic Acid," *Journal of Polymer Research*, 1996, vol. 3, No. 2, pp. 97-104.
Apr. 19, 2011 Supplementary European Search Report issued in European Patent Application No. 06842980.2.
Mar. 14, 2011 Korean Office Action in Korean Patent Application No. 2009-7012444 (with English-language translation).
Feb. 27, 2007 International Search Report issued in International Application No. PCT/JP2006/325472.

* cited by examiner

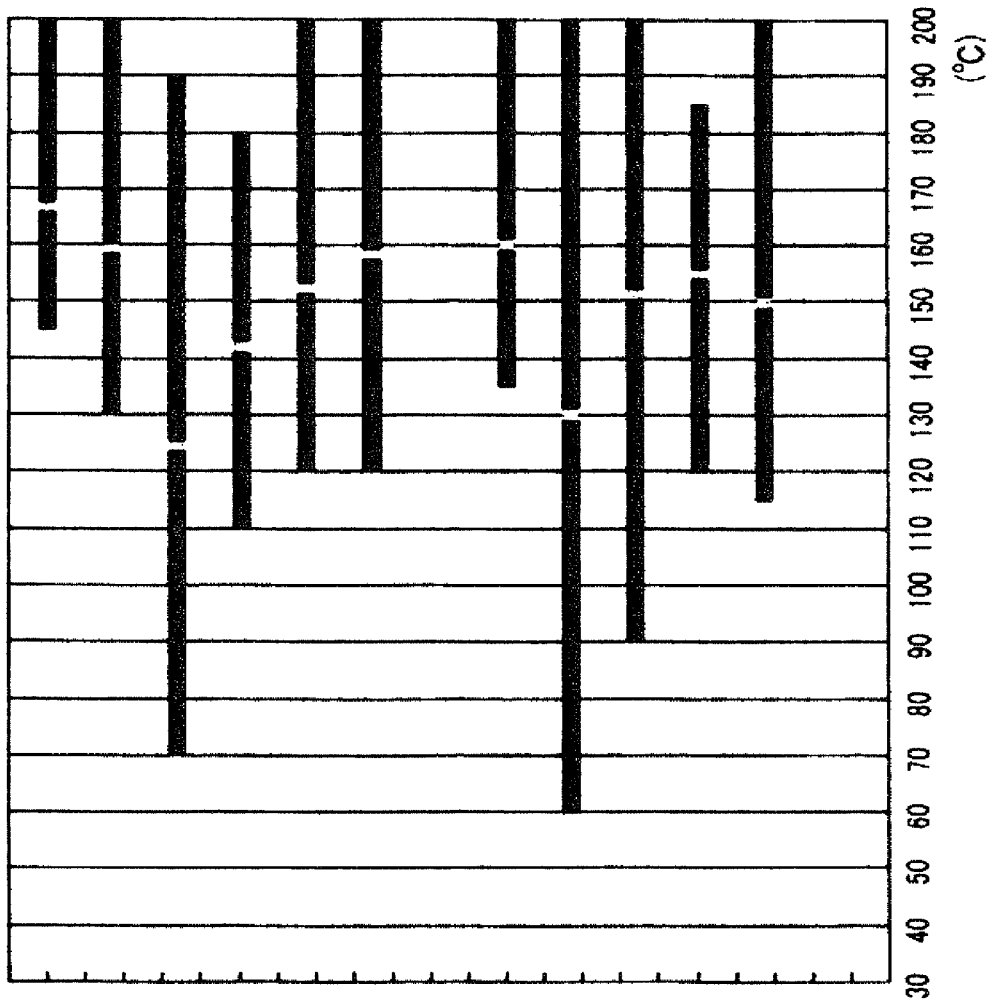

FIG. 20

Example 1
(5-nitroisophthalic acid-2E4MZ)
Example 2
(5-tBu-isophthalic acid-2E4MZ)
Comparative example 1
(2E4MZ)
Comparative example 2
(TEP-2E4MZ)
Comparative example 3
(isophthalic acid-2E4MZ)
Comparative example 4
(terephthalic acid-2E4MZ)

Example 4
(5-nitroisophthalic acid-2MZ)
Comparative example 5
(2MZ)
Comparative example 6
(TEP-2MZ)
Comparative example 7
(3,5-dihydroxybenzoic acid-2MZ)
Comparative example 8
(isophthalic acid-2MZ)

CLATHRATE COMPOUND, CURING CATALYST, COMPOSITION FOR FORMING CURED RESIN, AND CURED RESIN

CROSS-REFERENCE TO PRIOR APPLICATIONS

This is a continuation-in-part of application Ser. No. 12/448,245 filed Jun. 15, 2009, which is a National Stage Application of PCT/JP2006/325472 filed Dec. 21, 2006. The entire disclosures of the prior applications are hereby incorporated by reference herein in their entirety.

BACKGROUND

This disclosure relates to a novel clathrate compound, a curing catalyst containing the clathrate compound, a composition for forming a cured resin that uses the curing catalyst, a method of producing a cured resin that uses the composition for forming a cured resin, and a cured resin obtained using the production method.

Epoxy resins have excellent mechanical properties and thermal properties, and are therefore widely used in all manner of fields. An imidazole is typically used as the curing catalyst for curing these epoxy resins, but in epoxy resin-imidazole mixed liquids, curing initiation tends to be very fast, which creates a problem in that the one-pot stability is extremely poor.

Accordingly, as an alternative curing agent, the use of an acid addition salt of an imidazole obtained by adding a hydroxybenzoic acid to an imidazole (see Patent Document 1), and the use of a clathrate of a tetrakisphenol compound (such as 1,1,2,2-tetrakis(4-hydroxyphenyl)ethane (hereafter abbreviated as "TEP")) and an imidazole (see Patent Document 2) have been proposed. These acid addition salts of an imidazole and clathrates do provide a certain amount of effect, but the development of additional catalysts having either similar functionality or superior functionality has been keenly sought.

Patent Document 1:
Japanese Examined Patent Application, Second Publication No. Hei 04-2638
Patent Document 2:
Japanese Unexamined Patent Application, First Publication No. Hei 11-71449

SUMMARY

An object of this disclosure is to provide a curing catalyst (a clathrate compound) for which the curing reaction can be suppressed at low temperatures, allowing an improvement in the one-pot stability, but which can effectively cure a resin upon heat treatment. Furthermore, this disclosure also provides a composition for forming a cured resin that uses the above curing catalyst, a method of producing a cured resin that uses the composition for forming a cured resin, and a cured resin obtained using the production method.

As a result of intensive research aimed at achieving the above objects, the inventors of the present invention discovered that the above objects could be achieved by using a clathrate compound containing at least a specific imidazole and a specific acid, and the inventors were therefore able to complete the present invention.

In other words, the present invention relates to:
(1) a clathrate compound comprising:
an isophthalic acid compound represented by formula (I) shown below:

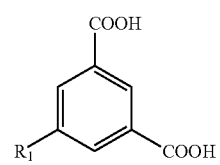

where $R_1$ represents a C1 to C6 alkyl group, a C1 to C6 alkoxy group, a nitro group, or a hydroxyl group; and
an imidazole compound represented by formula (II) shown below:

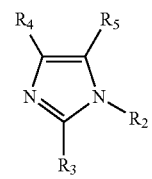

where:
$R_2$ represents a hydrogen atom, a C1 to C10 alkyl group, a phenyl group, a benzyl group, or a cyanoethyl group, and
$R_3$ to $R_5$ each independently represents:
a hydrogen atom, a nitro group, or a halogen atom, or
a C1 to C20 alkyl group that may have a substituent, a phenyl group that may have a substituent, a benzyl group that may have a substituent, or a C1 to C20 acyl group that may have a substituent;

(2) the clathrate compound disclosed in (1) above, wherein the isophthalic acid compound represented by formula (I) is 5-t-butylisophthalic acid, 5-hydroxyisophthalic acid, or 5-nitroisophthalic acid;

(3) the clathrate compound disclosed in (1) or (2) above, wherein the imidazole compound represented by formula (II) is imidazole, 2-ethyl-4-methylimidazole, 2-methylimidazole, 2-n-butylimidazole, 1-benzyl-2-methylimidazole, 2-heptadecylimidazole, 2-undecylimidazole or 2-phenyl-4-methyl-5-hydroxymethylimidazole;

(4) the clathrate compound disclosed in any one of (1) to (3) above, wherein $R_2$ is a hydrogen atom;

(5) the clathrate compound disclosed in any one of (1) to (4) above, wherein the compound is in a powdered form;

(6) a curing catalyst for an epoxy resin, comprising a clathrate compound disclosed in (1) above;

(7) a curing catalyst for an epoxy resin, comprising a clathrate compound disclosed in (2) above;

(8) a curing catalyst for an epoxy resin, comprising a clathrate compound disclosed in (3) above;

(9) a curing catalyst for an epoxy resin, comprising a clathrate compound disclosed in (4) above;

(10) a curing catalyst for an epoxy resin, comprising a clathrate compound disclosed in (5) above.

Furthermore, the present invention also relates to:
(11) a method for producing a clathrate compound, comprising:
dissolving or suspending in a solvent at least an isophthalic acid compound represented by formula (I) shown below:

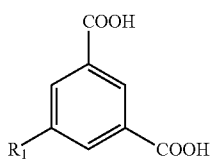

(I)

where $R_1$ represents a C1 to C6 alkyl group, a C1 to C6 alkoxy group, a nitro group, or a hydroxyl group, and
an imidazole compound represented by formula (II):

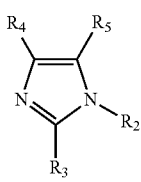

(II)

where:
$R_2$ represents a hydrogen atom, a C1 to C10 alkyl group, a phenyl group, a benzyl group, or a cyanoethyl group, and
$R_3$ to $R_5$ each independently represents:
a hydrogen atom, a nitro group, or a halogen atom, or
a C1 to C20 alkyl group, a phenyl group that may have a substituent, a benzyl group that may have a substituent, or a C1 to C20 acyl group that may have a substituent; and
subsequently conducting heating;
(12) the method disclosed in (11) above, further comprising performing a crystallization after heating.
In addition, the present invention also relates to:
(13) a clathrate compound comprising a host compound represented by formula (I) shown below:

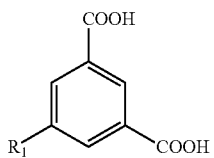

(I)

where $R_1$ represents a C4 alkyl group, a nitro group, or a hydroxyl group; and
the clathrate compound forms a lattice structure within at least a portion of the host compound.
By using a curing catalyst (clathrate compound) of the present invention, the curing reaction can be suppressed at low temperatures, allowing an improvement in the one-pot stability, whereas a resin can be cured effectively by conducting a heat treatment.

BRIEF DESCRIPTION OF THE DRAWINGS

FIG. 20 is a chart showing, in graphic form, the values for the reaction start temperature, the peak top, and the reaction end temperature read from the charts shown in FIG. 2 (Example 1), FIG. 5 (Example 2) and FIG. 8 (Example 4), as well as the same values for the Comparative Examples 1-8 also shown in graphic form.

DETAILED DESCRIPTION OF EMBODIMENTS

Figure 1:
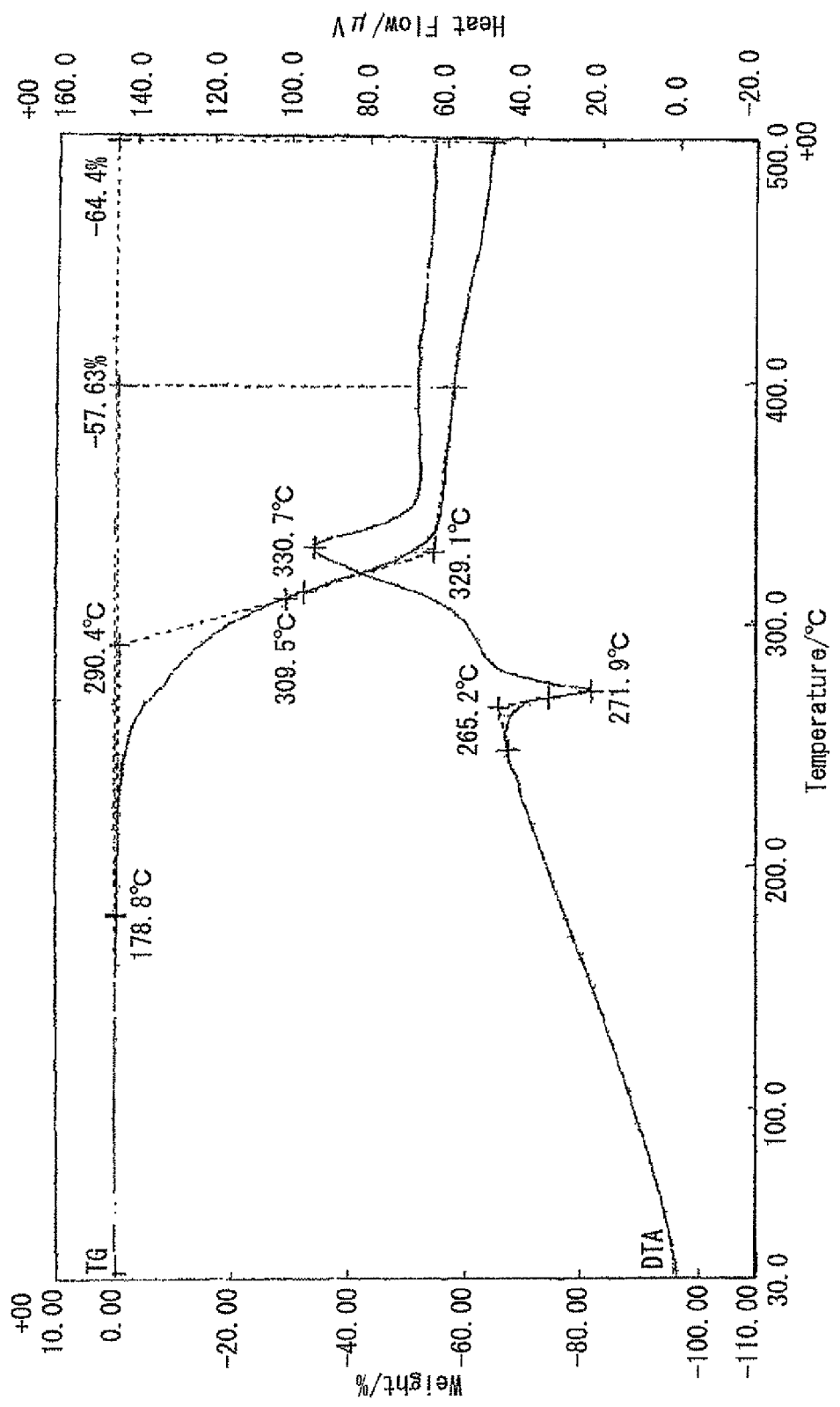
FIG. 1 is a thermal analysis (TG/DTA) chart for a clathrate according to Example 1.

There are no particular restrictions on the clathrate compound of the present invention, provided it includes at least an isophthalic acid compound represented by formula (I) (the host) and an imidazole compound represented by formula (II) (the guest). The compound may also include a third component such as a solvent, although the quantity of this third component is preferably not more than 40 mol %, more preferably 35 mol % or less, still more preferably 20 mol % or less, and still more preferably 10 mol % or less. A clathrate compound that does not include a third component and is composed solely of the isophthalic acid compound represented by formula (I) and the imidazole compound represented by formula (II) is the most desirable. In the present invention, a "clathrate compound" describes a compound in which two, or three or more, different types of molecule are bonded together via bonds other than covalent bonds, and preferably describes a crystalline compound in which two, or three or more, different types of molecule are bonded together via bonds other than covalent bonds. σ-Bonding, π-bonding, metal to metal bonding and agostic interactions are the covalent bonds. A clathrate compound containing an isophthalic acid compound represented by formula (I) and an imidazole compound represented by formula (II) can also be described as a salt formed from the isophthalic acid compound of formula (I) and the imidazole compound represented by formula (II).

The clathrate compound can be used as a resin curing agent for polyester resins, epoxy resins and epoxy-polyester resins and the like, and is particularly ideal as a curing agent for epoxy resins. Furthermore, the clathrate compound may be in a liquid form prepared by dissolving the compound in a solvent, but is preferably in a powdered form (precipitated from within a solvent). If the compound is in a powdered form, then it may also be used in powdered paints and the like.

A description of the isophthalic acid compound represented by formula (I) is presented below. In formula (I), $R_1$ represents a C1 to C6 alkyl group, C1 to C6 alkoxy group, nitro group, or hydroxyl group.

The C1 to C6 alkyl group is preferably a C1 to C4 alkyl group, and may have a substituent. Specific examples of the C1 to C6 alkyl group include a methyl group, ethyl group, propyl group, isopropyl group, cyclopropyl group, butyl group, isobutyl group, s-butyl group, t-butyl group, cyclobutyl group, cyclopropylmethyl group, pentyl group, isopentyl group, 2-methylbutyl group, neopentyl group, 1-ethylpropyl group, hexyl group, isohexyl group, 4-methylpentyl group, 3-methylpentyl group, 2-methylpentyl group, 1-methylpentyl group, 3,3-dimethylbutyl group, 2,2-dimethylbutyl group, 1,1-dimethylbutyl group, 1,2-dimethylbutyl group, 1,3-dimethylbutyl group, 2,3-dimethylbutyl group, 1-ethylbutyl group and 2-ethylbutyl group.

The C1 to C6 alkoxy group is preferably a C1 to C4 alkoxy group, and may have a substituent. Specific examples of the C1 to C6 alkoxy group include a methoxy group, ethoxy group, propoxy group, isopropoxy group, butoxy group, isobutoxy group, s-butoxy group, t-butoxy group, pentoxy group, isopentoxy group, 2-methylbutoxy group, 1-ethylpropoxy group, 2-ethylpropoxy group, neopentoxy group, hexyloxy group, 4-methylpentoxy group, 3-methylpentoxy group, 2-methylpentoxy group, 3,3-dimethylbutoxy group, 2,2-dimethylbutoxy group, 1,1-dimethylbutoxy group, 1,2-dimethylbutoxy group, 1,3-dimethylbutoxy group and 2,3-dimethylbutoxy group.

Specific examples of preferred compounds for the isophthalic acid compound represented by formula (I) include 5-t-butylisophthalic acid, 5-hydroxylisophthalic acid, and 5-nitroisophthalic acid.

Next is a description of the imidazole compound represented by formula (II). In formula (II), $R_2$ represents a hydrogen atom, a C1 to C10 alkyl group, a phenyl group, a benzyl group or a cyanoethyl group, and of these, a hydrogen atom is preferred.

The C1 to C10 alkyl group is preferably a C1 to C6 alkyl group, and may have a substituent. Specific examples of the C1 to C10 alkyl group include the alkyl groups listed above, as well as a heptyl group, octyl group, nonyl group and decyl group. Further, the phenyl group and benzyl group may also have a substituent.

$R_3$ to $R_5$ each independently represents a hydrogen atom, nitro group, halogen atom, or a C1 to C20 alkyl group that may have a substituent, a phenyl group that may have a substituent, a benzyl group that may have a substituent or a C1 to C20 acyl group that may have a substituent, preferably each independently represents a hydrogen atom, nitro group, halogen atom, or a C1 to C17 alkyl group, phenyl group, benzyl group or C1 to C17 acyl group that may have a substituent, and more preferably each independently represents a hydrogen atom, nitro group, halogen atom, or a C1 to C10 alkyl group, phenyl group, benzyl group or C1 to C10 acyl group that may have a substituent. The C1 to C20 alkyl group is as described above. The C1 to C20 acyl group that may have a substituent is preferably a C1 to C10 acyl group that may have a substituent, and is more preferably a C1 to C6 acyl group that may have a substituent. Specific examples include a formyl group, a acetyl group, a propionyl group, a butyryl group, a valeryl group or a benzoyl group.

There are no particular restrictions on the substituent that may be bonded to the alkyl group, phenyl group, benzyl group or acyl group, provided that a solid compound can be obtained that contains at least the isophthalic acid compound represented by formula (I) and the imidazole compound represented by formula (II) as structural elements. One example of a preferred substituent is a hydroxyl group.

Specific examples of the imidazole compound represented by formula (II) include imidazole, 2-ethyl-4-methylimidazole, 2-methylimidazole, 2-n-butylimidazole, 1-benzyl-2-methylimidazole, 2-heptadecylimidazole, 2-undecylimidazole, 2-phenyl-4-methyl-5-hydroxymethylimidazole, 2-phenylimidazole, 2-phenyl-4-methylimidazole, 1-benzyl-2-phenylimidazole, 1,2-dimethylimidazole, 1-cyanoethyl-2-methylimidazole, 1-cyanoethyl-2-ethyl-4-methylimidazole, 1-cyanoethyl-2-undecylimidazole, 1-cyanoethyl-2-phenylimidazole and 2-phenyl-4,5-dihydroxymethylimidazole. In terms of the ease with which a powdered clathrate compound can be formed, imidazole, 2-ethyl-4-methylimidazole, 2-methylimidazole, 2-n-butylimidazole, 1-benzyl-2-methylimidazole, 2-heptadecylimidazole, 2-undecylimidazole and 2-phenyl-4-methyl-5-hydroxymethylimidazole are preferred, and if the one-pot stability is also taken into consideration, then imidazole, 2-ethyl-4-methylimidazole are particularly desirable.

The above type of clathrate compound can be obtained by adding the isophthalic acid compound represented by formula (I) and the imidazole compound represented by formula (II) to a solvent, and then conducting either a heat treatment or a heated reflux treatment, under stirring if required, to precipitate the clathrate compound. Furthermore, depending on the variety of isophthalic acid compound represented by formula (I) and the variety of the imidazole compound represented by formula (II), precipitation via the same operation as that described above may yield a crystalline compound.

In order to facilitate dissolution within the solvent, the isophthalic acid compound represented by formula (I) and the imidazole compound represented by formula (II) are preferably dissolved separately in solvents, and the resulting solutions are then preferably mixed. Examples of solvents that may be used include water, methanol, ethanol, ethyl acetate, methyl acetate, diethyl ether, dimethyl ether, acetone, methyl ethyl ketone and acetonitrile. In terms of the proportions added of the isophthalic acid compound represented by formula (I) and the imidazole compound represented by formula (II) during production of the clathrate compound, the amount added of the imidazole compound represented by formula (II) (the guest) is preferably within a range from 0.1 to 5.0 mol, and more preferably from 0.5 to 3.0 mol, relative to 1 mol of the isophthalic acid compound represented by formula (I) (the host).

There are no particular restrictions on the clathrate compound, provided it can be obtained after dissolving or suspending at least the isophthalic acid compound represented by formula (I) and the imidazole compound represented by formula (II) in a solvent and conducting heating. The compound may also include a third component such as a solvent, although the quantity of this third component is preferably not more than 40 mol %, more preferably 35 mol % or less, still more preferably 20 mol % or less, and still more preferably 10 mol % or less, and a compound that does not contain a third component is the most desirable.

Although there are no particular restrictions on the clathrate compound invention, provided it can be obtained after dissolving or suspending at least the isophthalic acid compound represented by formula (I) and the imidazole compound represented by formula (II) in a solvent and conducting heating, the compound is preferably a compound that can be obtained by dissolving or suspending at least the isophthalic acid compound represented by formula (I) and the imidazole compound represented by formula (II) in a solvent, conducting heating, and then precipitating the compound, and is more preferably a crystalline compound that can be obtained by dissolving or suspending at least the isophthalic acid compound represented by formula (I) and the imidazole compound represented by formula (II) in a solvent, conducting heating, and then crystallizing the compound.

The isophthalic acid compound represented by formula (I) and the imidazole compound represented by formula (II) are as described above. There are no particular restrictions on the solvent, provided it does not hinder the process of obtaining the clathrate compound by dissolving or suspending the isophthalic acid compound represented by formula (I) and the imidazole compound represented by formula (II) in a solvent and conducting heating, and an appropriate solvent can be selected in accordance with the isophthalic acid compound represented by formula (I) and the imidazole compound represented by formula (II) that are actually used. Specific examples of the solvent are as described above.

In terms of the proportions added of the isophthalic acid compound represented by formula (I) and the imidazole compound represented by formula (II) during production of the clathrate compound, the amount added of the imidazole compound represented by formula (II) is preferably within a range from 0.1 to 5.0 mol, and more preferably from 0.5 to 3.0 mol, relative to 1 mol of the isophthalic acid compound represented by formula (I).

During production of the clathrate compound, the isophthalic acid compound represented by formula (I) and the imidazole compound represented by formula (II) are dissolved or suspended in a solvent, and both compounds are preferably dissolved in the solvent. In those cases where both compounds are dissolved in a solvent, the entire amount of both compounds need not necessarily dissolve in the solvent, but at least a small portion of both compounds must dissolve in the solvent.

There are no particular restrictions on the heating conditions employed during production of the clathrate compound, provided that the compound can be obtained after dissolving at least the isophthalic acid compound represented by formula (I) and the imidazole compound represented by formula (II) in a solvent and conducting the heating. For example, heating may be conducted at a temperature within a range from 40 to 120° C., and is preferably conducted within a range from 50 to 90° C.

Furthermore, the heating conducted during production of the clathrate compound need not necessarily be conducted while stirring the solution or suspension containing the isophthalic acid compound represented by formula (I) and the imidazole compound represented by formula (II), but the heating is preferably conducted while the solution or suspension is stirred, and is more preferably conducted under heated reflux conditions.

During the production of the compound, there are no particular restrictions on the step conducted after dissolving or suspending at least the isophthalic acid compound represented by formula (I) and the imidazole compound represented by formula (II) in a solvent and conducting heating, provided this subsequent step yields a solid compound containing at least the isophthalic acid compound represented by formula (I) and the imidazole compound represented by formula (II) as structural elements. For example, after dissolving the isophthalic acid compound represented by formula (I) and the imidazole compound represented by formula (II) in a solvent and conducting heating, the solid compound may be precipitated by simply stopping the heating treatment, but the solution is preferably left to stand over night at room temperature after the heating is stopped. After precipitation of the solid compound, filtering and drying can be used to obtain the target compound. Furthermore, depending on factors such as the types of the isophthalic acid compound represented by formula (I) used and the types of the imidazole compound represented by formula (II) used, the same operations as those described in the above steps for obtaining the solid compound may yield a crystalline compound.

Provided a compound is the same as the compound of the present invention, it is deemed to be incorporated within the present invention, even if it is not obtained after dissolving at least an isophthalic acid compound represented by formula (I) and an imidazole compound represented by formula (II) in a solvent and conducting heating.

There are no particular restrictions on the curing catalyst for an epoxy resin according to the present invention, provided it includes a clathrate compound of the present invention or a compound of the present invention, and for example, the catalyst may also include other epoxy resin curing catalysts.

Furthermore, there are no particular restrictions on the composition for forming a cured epoxy resin according to the present invention, provided the composition includes an epoxy resin (component (A)) and either a clathrate compound of the present invention or a compound of the present invention (component (B)). Component (B) is as described above.

As the epoxy resin of component (A), all manner of conventional polyepoxy compounds can be used, and specific examples include aromatic glycidyl ether compounds such as bis(4-hydroxyphenyl)propane diglycidyl ether, bis(4-hydroxy-3,5-dibromophenyl)propane diglycidyl ether, bis(4-hydroxyphenyl)ethane diglycidyl ether, bis(4-hydroxyphenyl)methane diglycidyl ether, resorcinol diglycidyl ether, phloroglucinol triglycidyl ether, trihydroxybiphenyl triglycidyl ether, tetraglycidylbenzophenone, bisresorcinol tetraglycidyl ether, tetramethylbisphenol A diglycidyl ether, bisphenol C diglycidyl ether, bisphenolhexafluoropropane diglycidyl ether, 1,3-bis[1-(2,3-epoxypropoxy)-1-trifluoromethyl-2,2,2-trifluoroethyl]benzene, 1,4-bis[1-(2,3-epoxypropoxy)-1-trifluoromethyl-2,2,2-trifluoromethyl]benzene, 4,4'-bis(2,3-epoxypropoxy)octafluorobiphenyl, and phenol novolak bisepoxy compounds; alicyclic polyepoxy compounds such as alicyclic diepoxy acetal, alicyclic diepoxy adipate, alicyclic diepoxy carboxylate, and vinylcyclohexene dioxide; glycidyl ester compounds such as diglycidyl phthalate, diglycidyl tetrahydrophthalate, diglycidyl hexahydrophthalate, dimethylglycidyl phthalate, dimethylglycidyl hexahydrophthalate, diglycidyl p-oxybenzoate, diglycidyl cyclopentane-1,3-dicarboxylate, and dimer acid glycidyl ester; glycidylamine compounds such as diglycidylaniline, diglycidyltoluidine, triglycidylaminophenol, tetraglycidyl-diaminodiphenylmethane, and diglycidyltribromoanaline; and heterocyclic epoxy compounds such as diglycidylhydantoin, glycidylglycidoxyalkylhydantoin, and triglycidyl isocyanurate.

The proportion of the imidazole compound represented by formula (II) within components (A) and (B) in the composition for forming a cured epoxy resin according to the present invention is preferably such that the amount of the imidazole compound represented by formula (II) within component (B) is within a range from 0.01 to 1.0 mol, more preferably from 0.1 to 1.0 mol, and still more preferably from 0.3 to 1.0 mol, relative to 1 mol of epoxy rings within the epoxy resin of component (A).

Further, the composition for forming a cured epoxy resin according to the present invention can be produced by mixing component (A) and component (B), and in order to ensure formation of a satisfactory mixed state, mixing is usually conducted under heating at a temperature of 60 to 100° C. In the production of the cured epoxy resin, the one-pot stability of the composition at this temperature is an important factor.

Furthermore, there are no particular restrictions on the method used for producing the cured epoxy resin of the present invention, provided the method includes curing the composition for forming a cured epoxy resin by conducting a heat treatment. The heating temperature employed during the heat treatment is typically within a range from 60 to 250° C. and preferably from 100 to 200° C., and the composition is preferably cured in a short period of time at such a temperature.

There are no particular restrictions on the host compound for the clathrate compound of the present invention, provided it is an isophthalic acid compound represented by formula (I) (wherein $R_1$ represents a nitro group, a hydroxyl or a C4 alkyl group), and the C4 alkyl group is preferably a t-butyl group.

As used herein, the host compound for the clathrate compound refers to a compound that undergoes bonding other than covalent bonding to one, or two or more, different types of molecules (such as a guest or solvent molecule) to form a compound, wherein this compound is capable of forming a clathrate lattice, and more preferably refers to a compound that undergoes bonding other than covalent bonding to one, or two or more, different types of molecules (such as a guest or solvent molecule) to form a crystalline compound, wherein this crystalline compound is capable of forming a clathrate lattice. Here, the "clathrate lattice" refers to either a structure in which molecules of the host compound are bonded together via bonding other than covalent bonding, and another molecule (such as a guest or solvent molecule) or a combination of another molecule and a host compound are bonded by some form of bonding other than covalent bonding within the spaces between two, or three or more, host compounds, or a structure in which the host compound is bonded to another molecule (such as a guest or solvent molecule) via bonding other than covalent bonding, and a host compound and/or another molecule (such as a guest or solvent molecule) are bonded by some form of bonding other than covalent bonding within the spaces between two, or three or more, of the host compounds bonded to other molecules. When preparing a clathrate compound using a host compound of the present invention, depending on the types of the guest compound, molecules of the guest compound may also bond together via some form of bonding other than covalent bonding, but such bonding has no effect on the host compound of the present invention acting as the host compound.

There are no particular restrictions on the shape of the clathrate lattice, and examples include tunnel-type lattices, layered lattices and network lattices.

The host compound of the present invention forms a lattice structure within at least a portion of the clathrate compound, and host compound molecules that do not form a clathrate lattice may be included within the clathrate compound, although the entire clathrate compound is preferably in the form of a clathrate lattice.

EXAMPLES

A more detailed description of the present invention is presented below based on a series of examples, although the technical scope of the present invention is in no way limited by these examples.

Example 1

Figure 2:
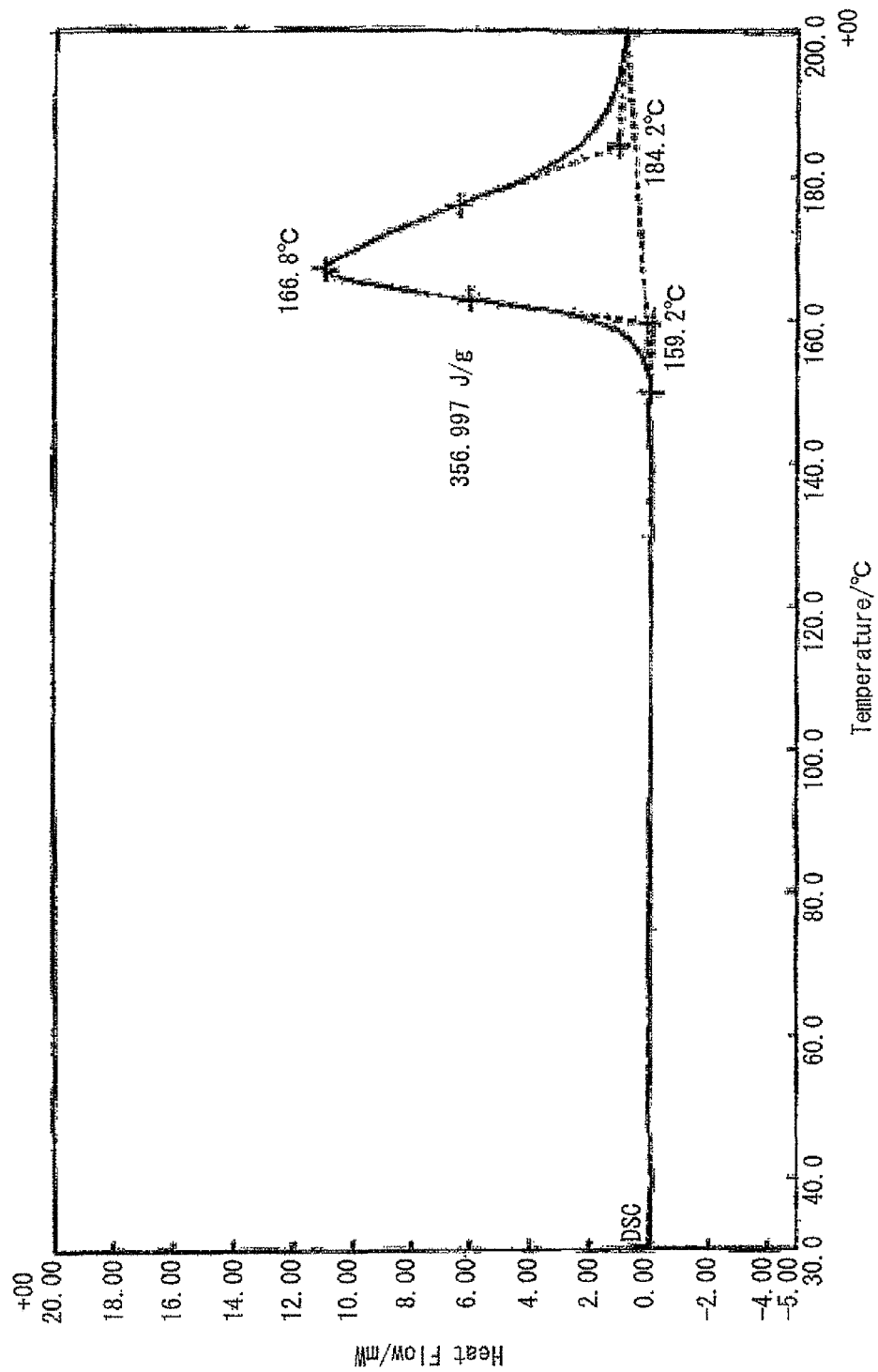
FIG. 2 is a thermal analysis (DSC) chart upon temperature variation for the clathrate according to Example 1.
Figure 3:
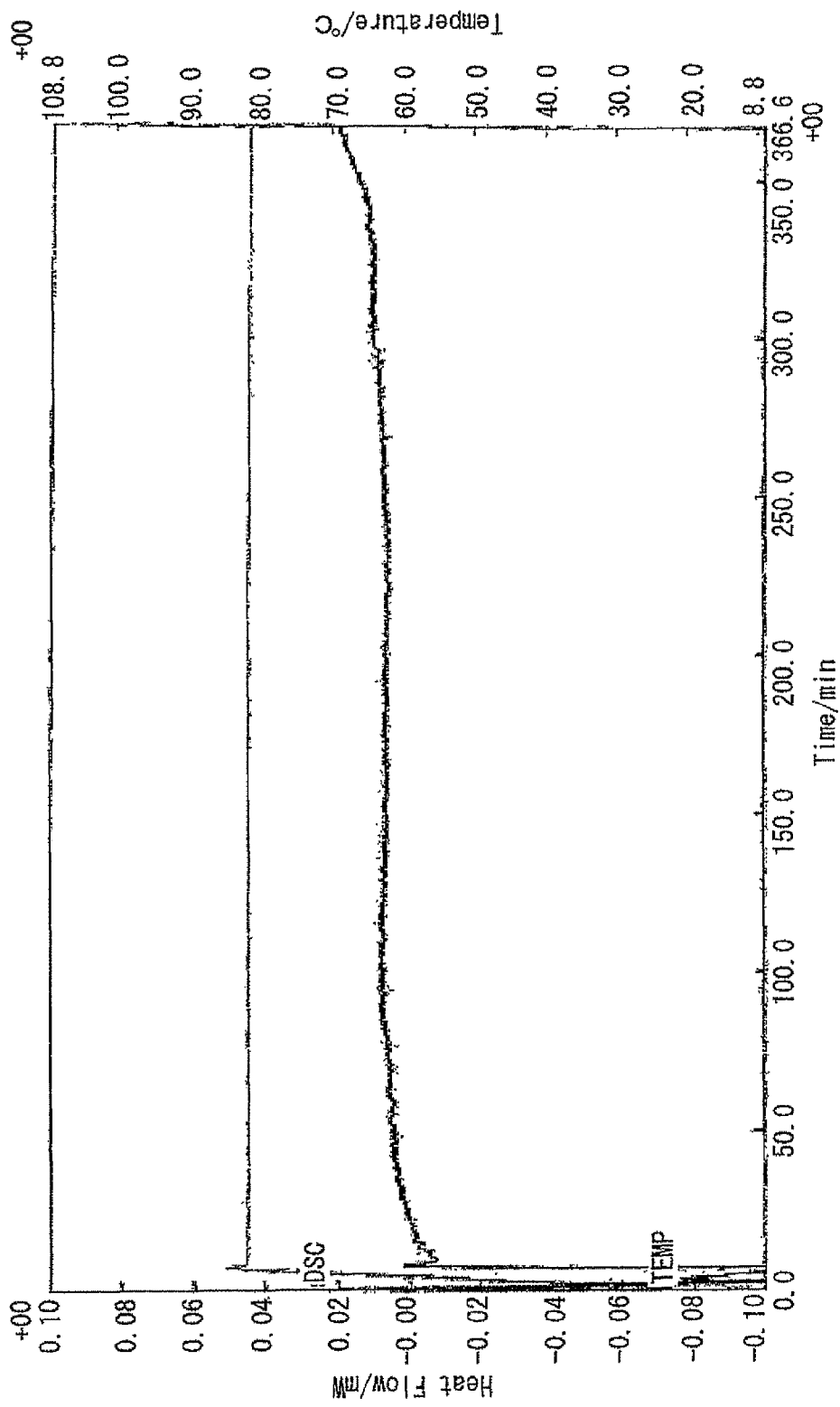
FIG. 3 is a thermal analysis (DSC) chart at a fixed temperature (80° C.) for the clathrate according to Example 1.
Figure 18:
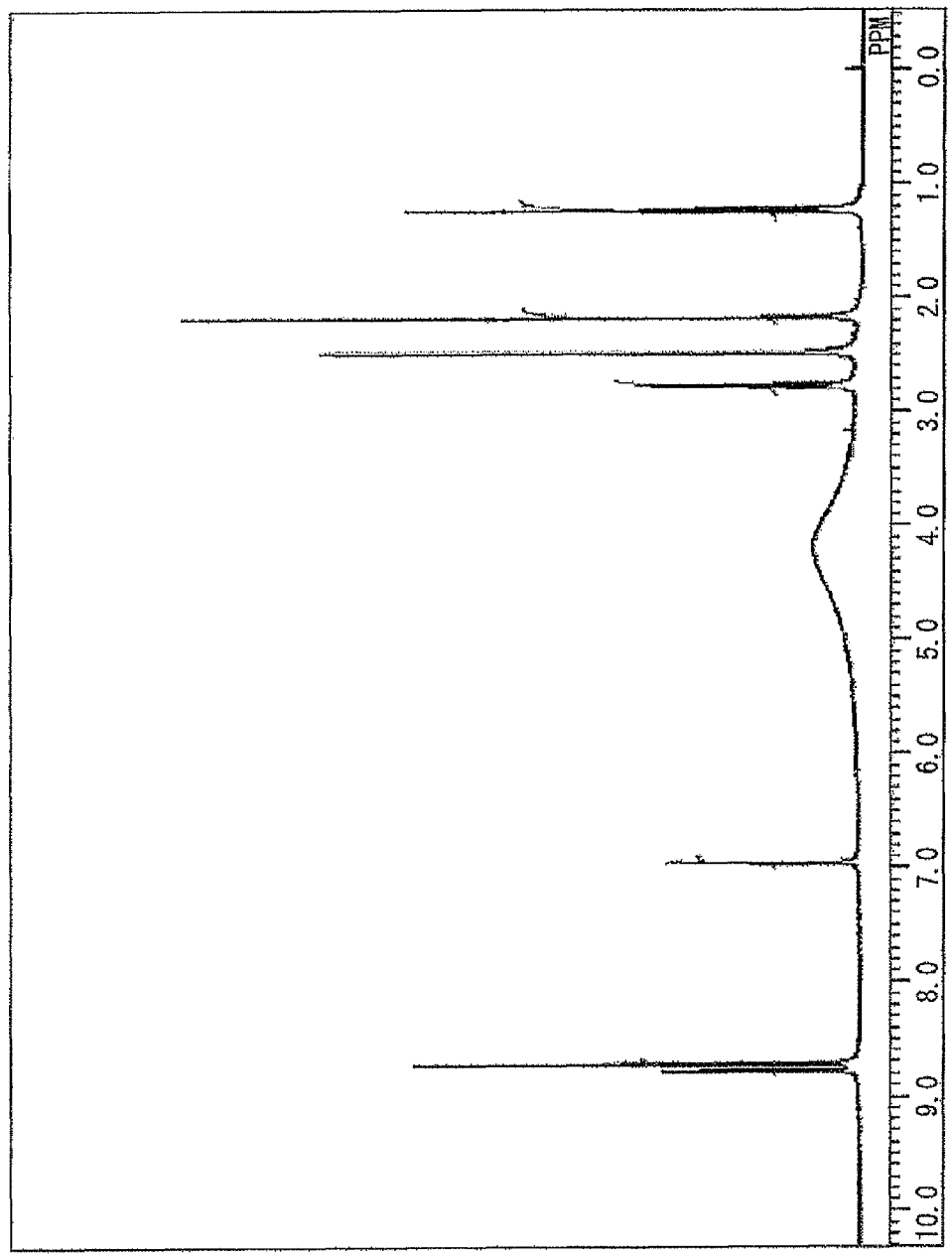
FIG. 18 is a $^1$H-NMR spectral chart for the clathrate according to Example 1 of the present invention.
Figure 19:
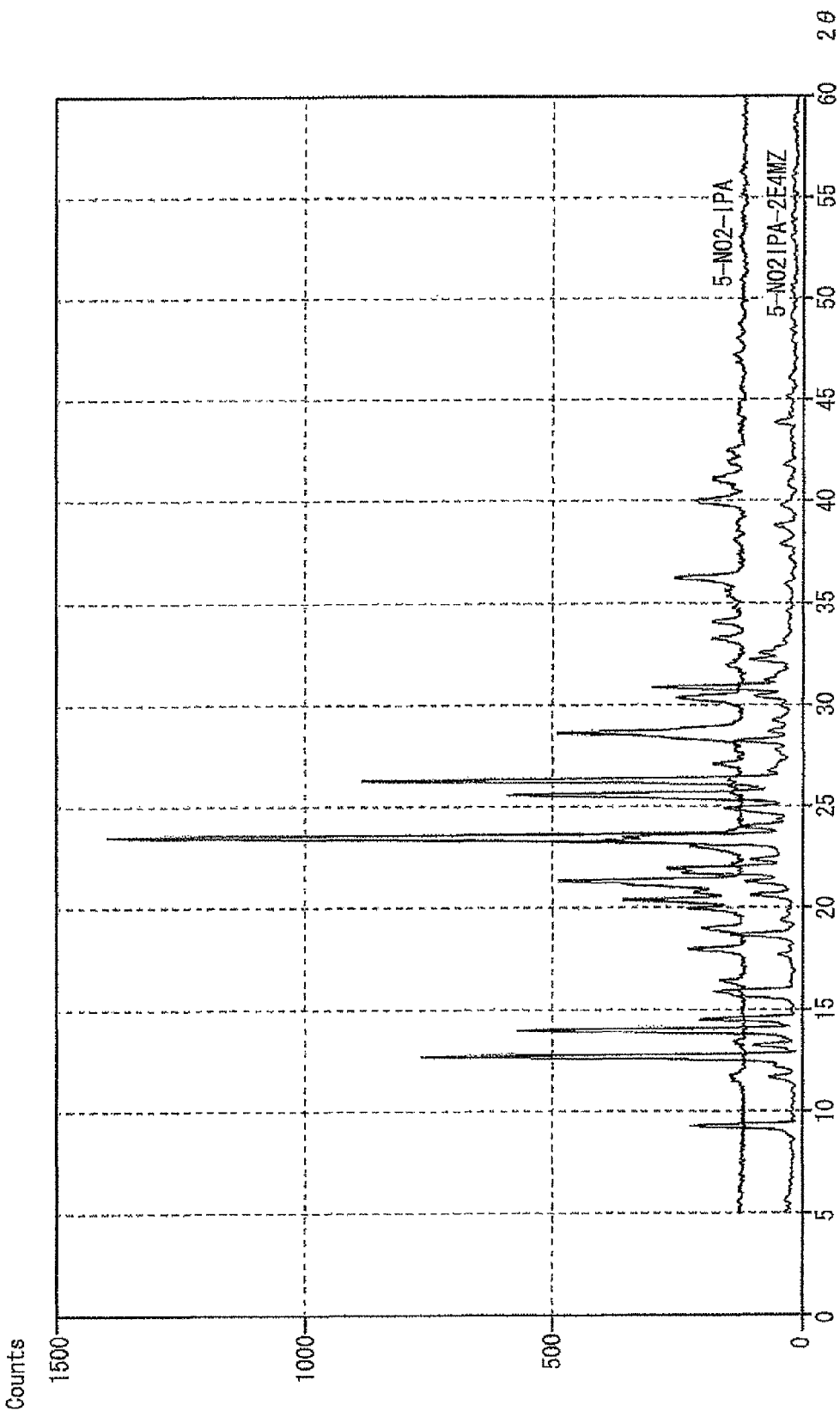
FIG. 19 illustrates X-ray diffraction patterns for the clathrate (5-NO2IPA-2E4MZ) according to Example 1 and 5-nitroisophthalic acid (5-NO2-IPA).

20 ml of a methanol solution containing 10 mmol (1.10 g) of 2-ethyl-4-methylimidazole was added to 20 ml of a methanol solution containing 5 mmol (1.05 g) of 5-nitroisophthalic acid under conditions of heated reflux with stirring. Although heating is subsequently stopped, crystals precipitate almost immediately, the mixture was left to stand overnight at room temperature, and then filtered and dried under vacuum, yielding a clathrate (0.5 g, 33%). Analysis of the obtained clathrate by NMR revealed 1:1 clathrate crystals. The $^1$H-NMR spectral chart and the X-ray diffraction pattern for the obtained clathrate (5-NO2IPA-2E4MZ) are shown in FIG. 18 and FIG. 19 respectively. For the purposes of comparison, the X-ray diffraction pattern for 5-nitroisophthalic acid (5-NO2-IPA) is also shown in FIG. 19. A thermal analysis (TG/DTA) chart for the obtained clathrate crystals is shown in FIG. 1. Furthermore, a thermal analysis (DSC) chart upon temperature variation for the obtained clathrate crystals is shown in FIG. 2, whereas a thermal analysis (DSC) chart at a fixed temperature (80° C.) is shown in FIG. 3.

Example 2

Figure 4:
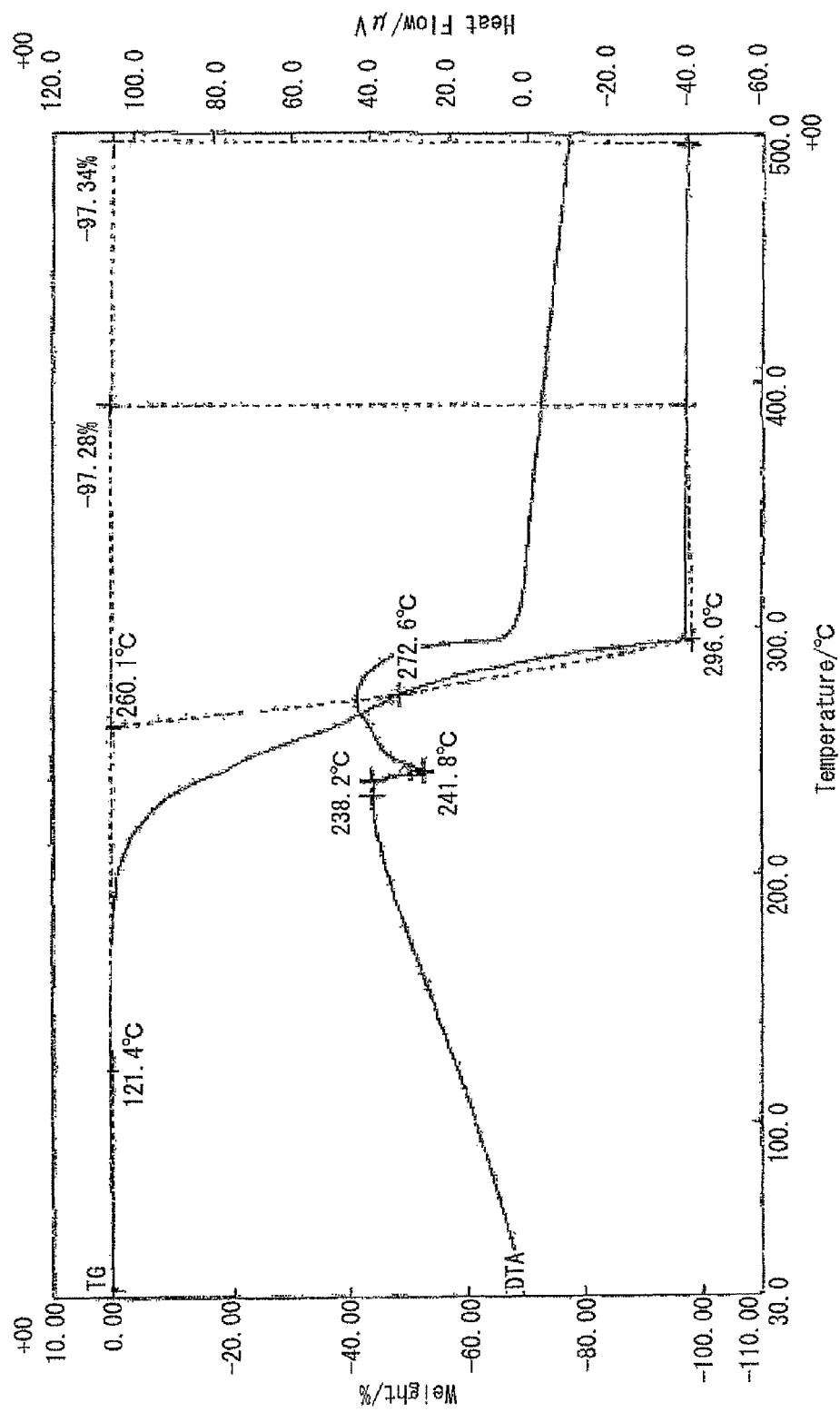
FIG. 4 is a thermal analysis (TG/DTA) chart for a clathrate according to Example 2.
Figure 5:
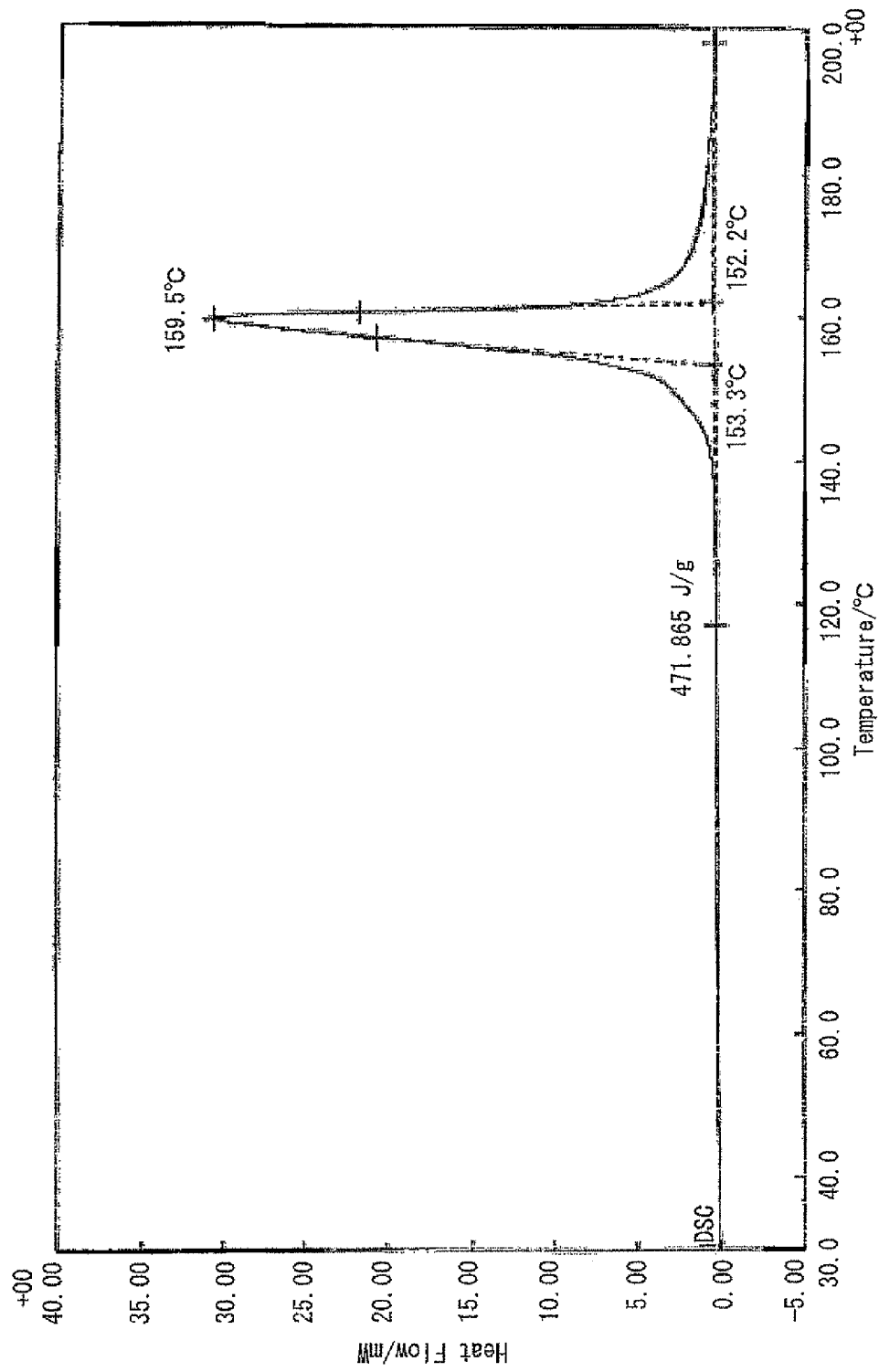
FIG. 5 is a thermal analysis (DSC) chart upon temperature variation for the clathrate according to Example 2.
Figure 6:
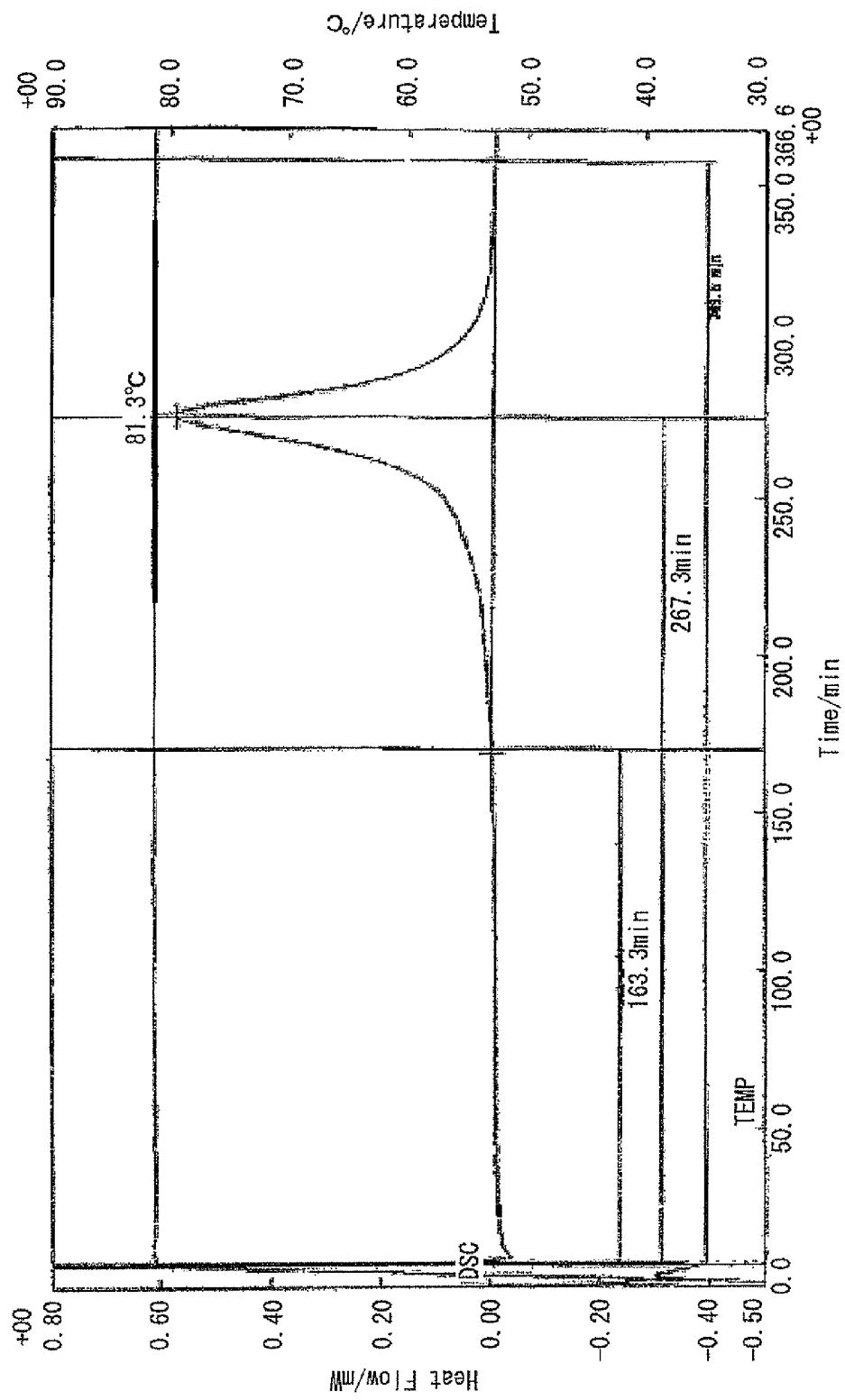
FIG. 6 is a thermal analysis (DSC) chart at a fixed temperature (80° C.) for the clathrate according to Example 2.

15 mmol (3.33 g) of 5-t-butylisophthalic acid and 18 mmol (1.98 g, 1.2 eq.) of 2-ethyl-4-methylimidazole were added to 60 ml of methanol, and the resulting mixture was stirred under heated reflux in a round-bottom flask for 30 minutes, thereby dissolving the crystals. Subsequently, the solution was left to stand at room temperature, and the crystals that precipitated from the solution were filtered and dried under vacuum, yielding a clathrate compound (2.34 g, 47%). Analysis of the obtained clathrate by NMR revealed 1:1 clathrate crystals. A thermal analysis (TG/DTA) chart for the obtained clathrate crystals is shown in FIG. 4. Furthermore, a thermal analysis (DSC) chart upon temperature variation for the obtained clathrate crystals is shown in FIG. 5, whereas a thermal analysis (DSC) chart at a fixed temperature (80° C.) is shown in FIG. 6.

Example 3

With the exception of altering the amount of 2-ethyl-4-methylimidazole to 16.5 mmol (1.81 g, 1.1 eq.), a clathrate was prepared in the same manner as Example 2 (2.08 g, 42%). Analysis of the obtained clathrate by NMR revealed 1:1 clathrate crystals, and a thermal analysis (TG/DTA) chart for the obtained clathrate crystals was the same as that for the crystals obtained in Example 2.

Example 4

Figure 7:
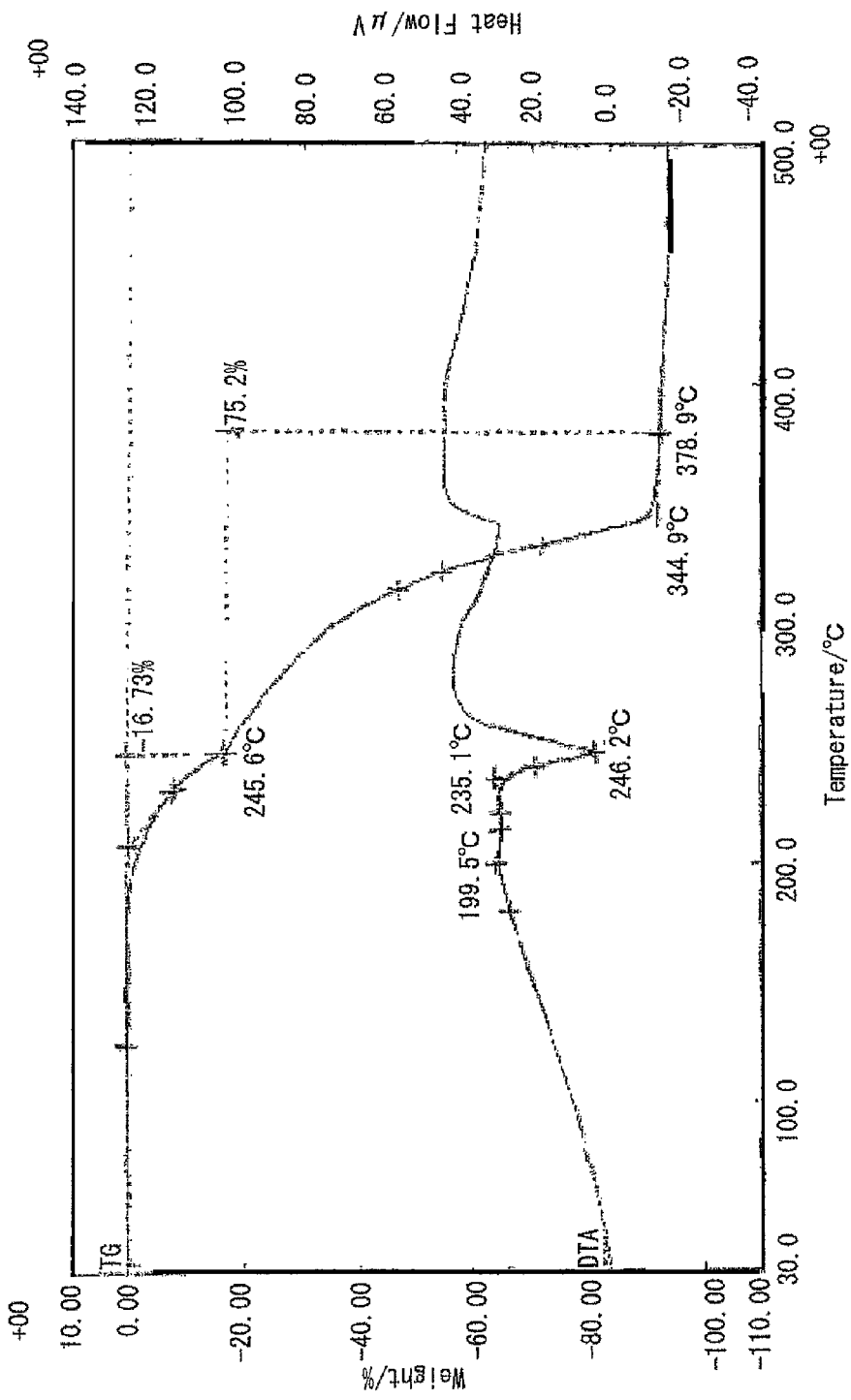
FIG. 7 is a thermal analysis (TG/DTA) chart for a clathrate according to an Example 4.
Figure 8:
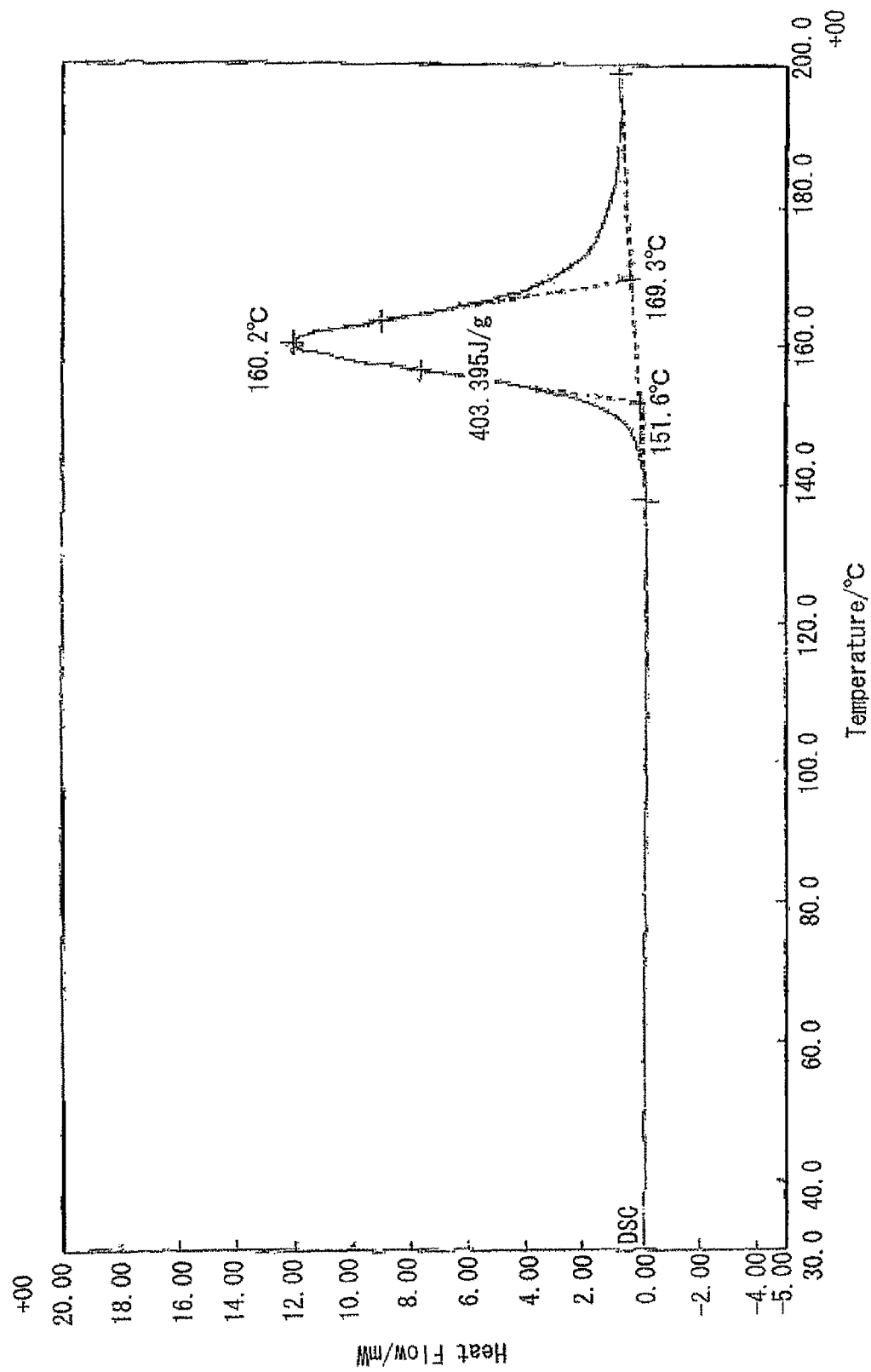
FIG. 8 is a thermal analysis (DSC) chart upon temperature variation for the clathrate according to Example 4.
Figure 9:
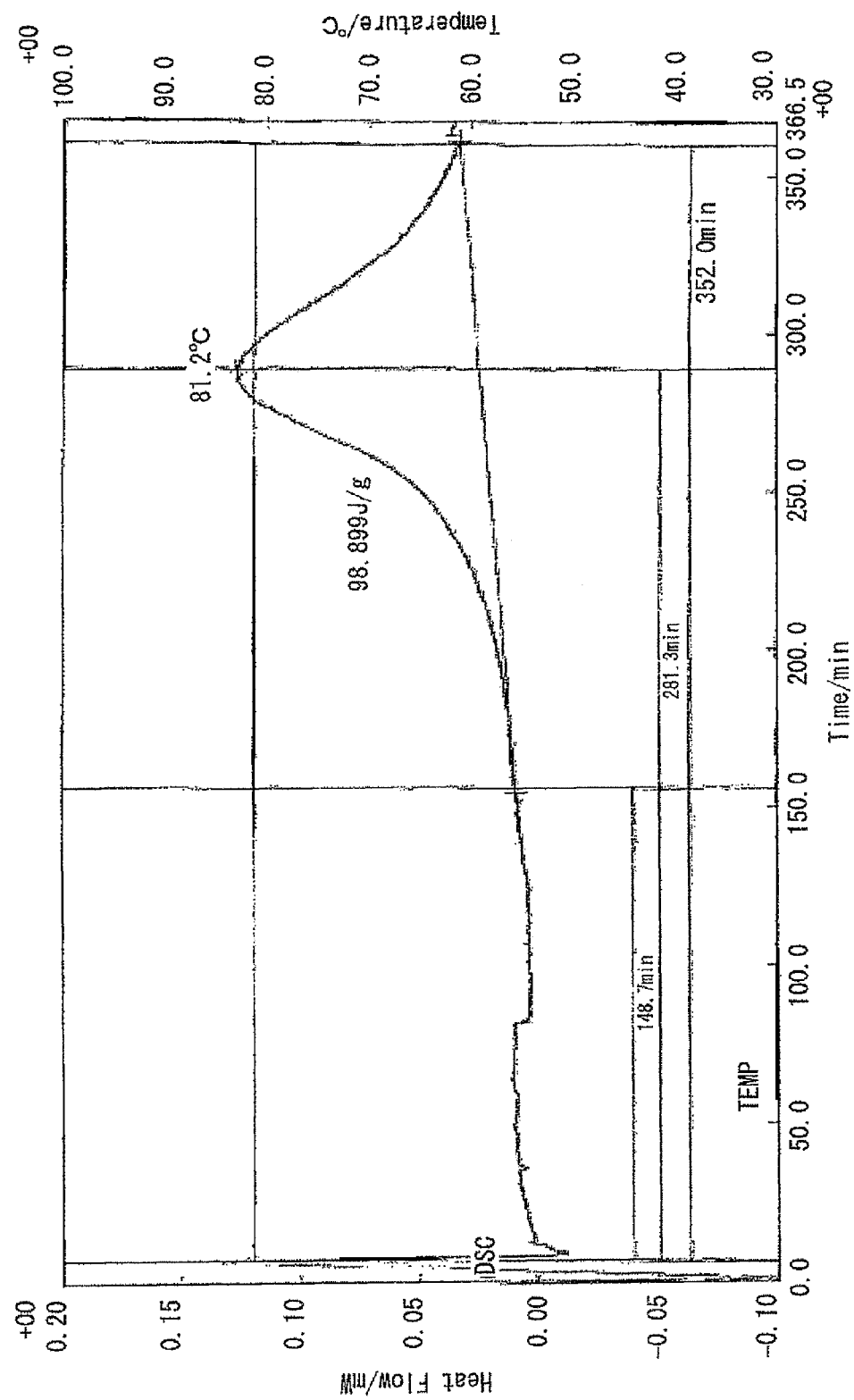
FIG. 9 is a thermal analysis (DSC) chart at a fixed temperature (80° C.) for the clathrate according to Example 4.

20 ml of a methanol solution containing 10 mmol (0.82 g) of 2-methylimidazole was added to 20 ml of a methanol solution containing 5 mmol (1.05 g) of 5-nitroisophthalic acid under conditions of heated reflux with stirring. Although heating is subsequently stopped, crystals precipitate almost immediately, the mixture was left to stand overnight at room temperature, and then filtered and dried under vacuum, yielding a clathrate (1.2 g, 64%). Analysis of the obtained clathrate by NMR revealed 1:1 clathrate crystals. A thermal analysis (TG/DTA) chart for the obtained clathrate crystals is shown in FIG. 7. Furthermore, a thermal analysis (DSC) chart upon temperature variation for the obtained clathrate crystals is shown in FIG. 8, whereas a thermal analysis (DSC) chart at a fixed temperature (80° C.) is shown in FIG. 9.

Example 5

5 mmol (1.06 g) of 5-nitroisophthalic acid and 5 mmol (1.11 g) of 2-undecylimidazole were added to 40 ml of acetone, and the resulting mixture was stirred under heat and then left to stand overnight. After standing overnight, the mixture was filtered and dried under vacuum, yielding 1.98 g of a clathrate (1:1 clathrate).

Figure 10:
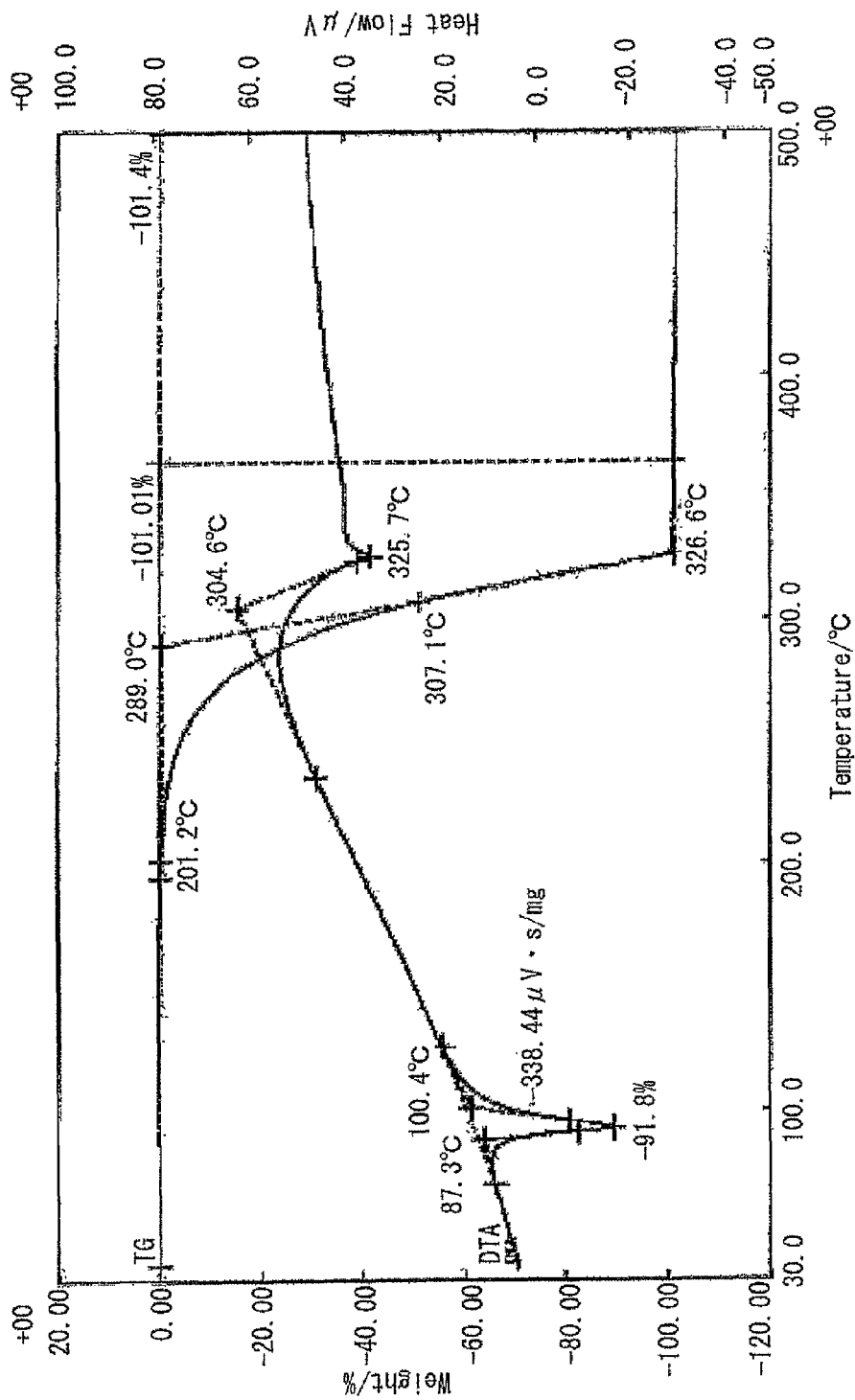
FIG. 10 is a thermal analysis (TG/DTA) chart for only 2-undecylimidazole.
Figure 11:
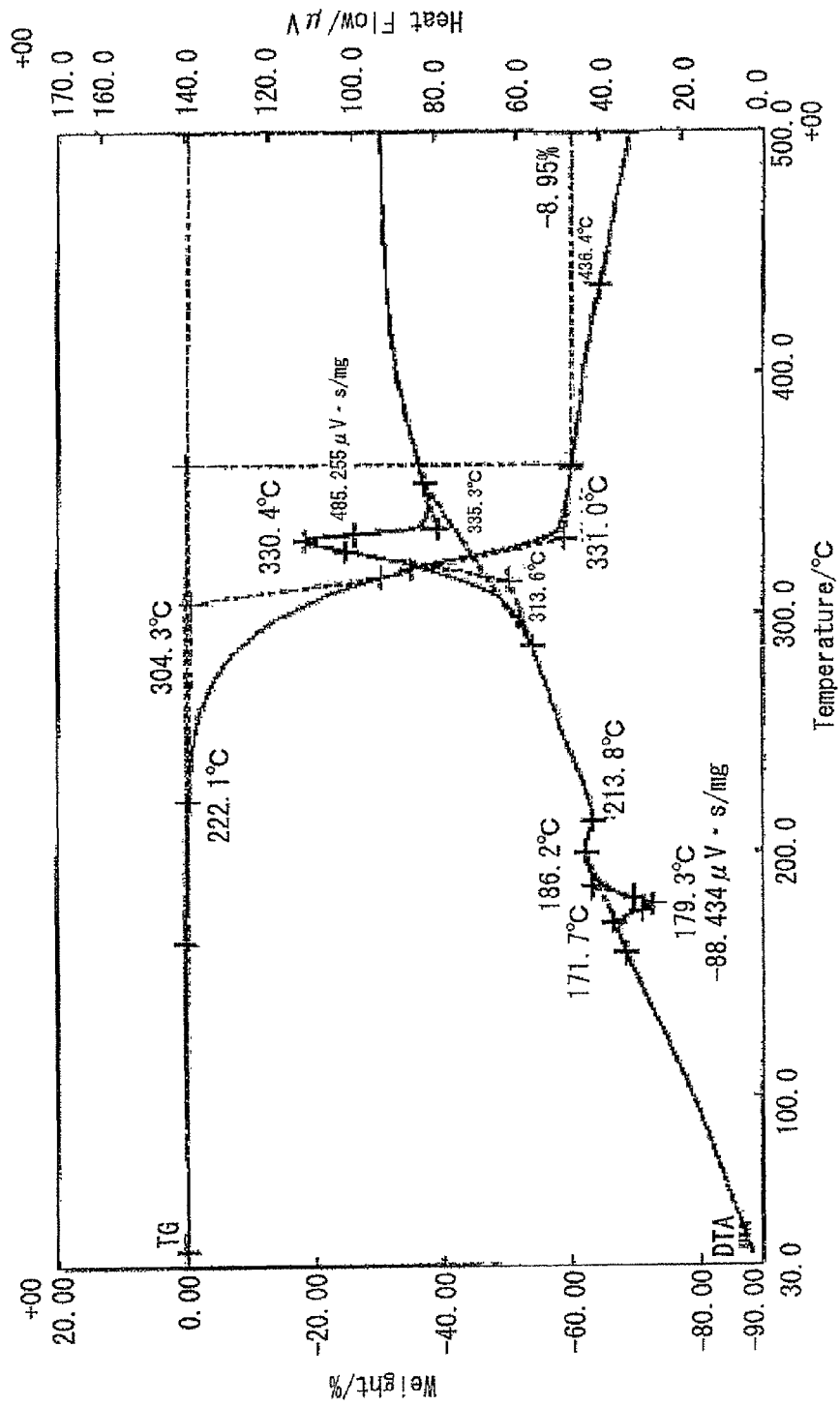
FIG. 11 is a thermal analysis (TG/DTA) chart for a clathrate according to an Example 5.

A thermal analysis (TG/DTA) chart for only 2-undecylimidazole is shown in FIG. 10, whereas a thermal analysis (TG/DTA) chart for the obtained clathrate crystals is shown in FIG. 11. It is thought that because the melting point for 2-undecylimidazole was not observed in the chart of FIG. 11, the obtained crystals are a clathrate compound.

Figure 12:
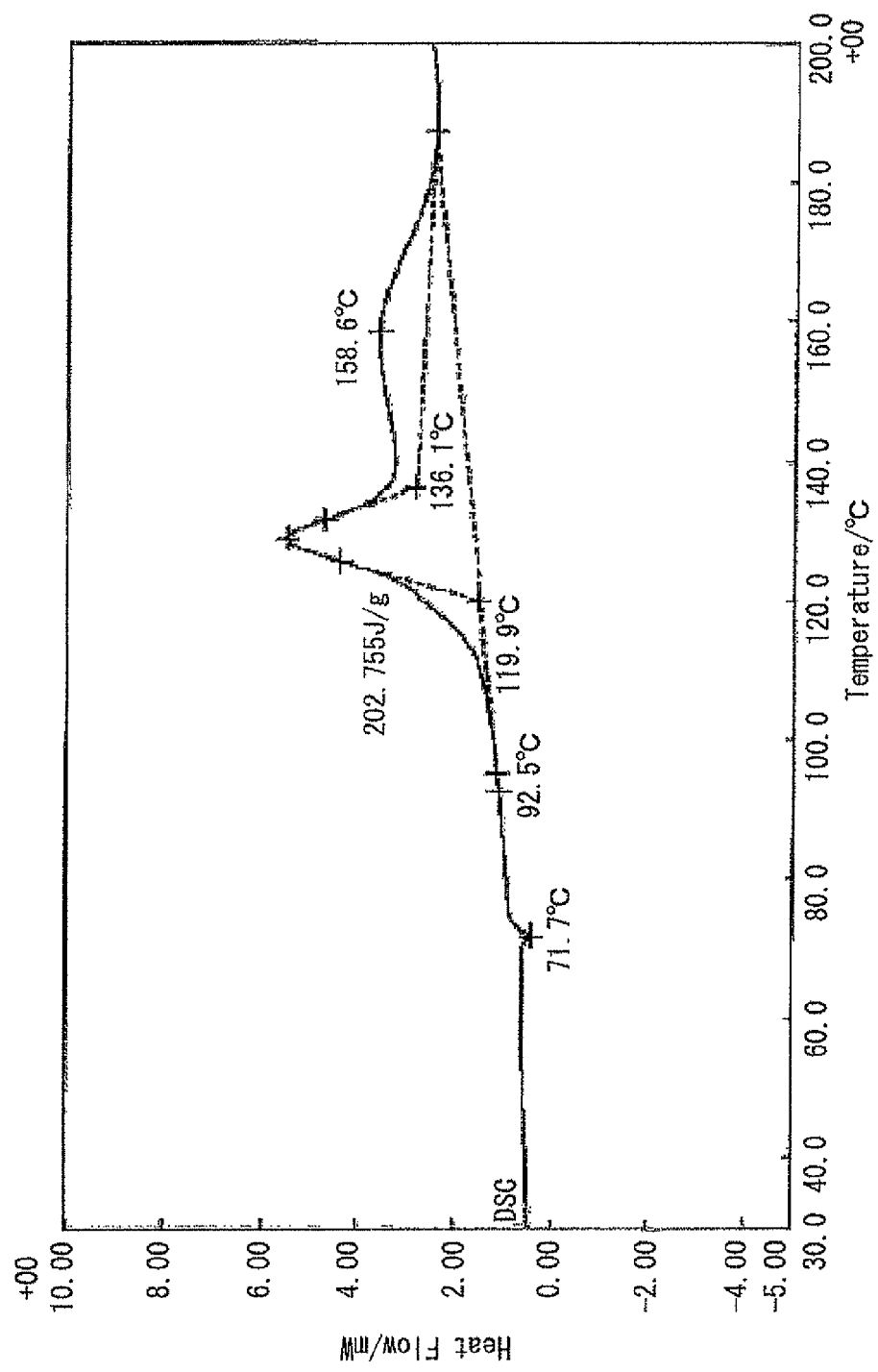
FIG. 12 is a thermal analysis (DSC) chart upon temperature variation for 2-undecylimidazole and an epoxy resin.
Figure 13:
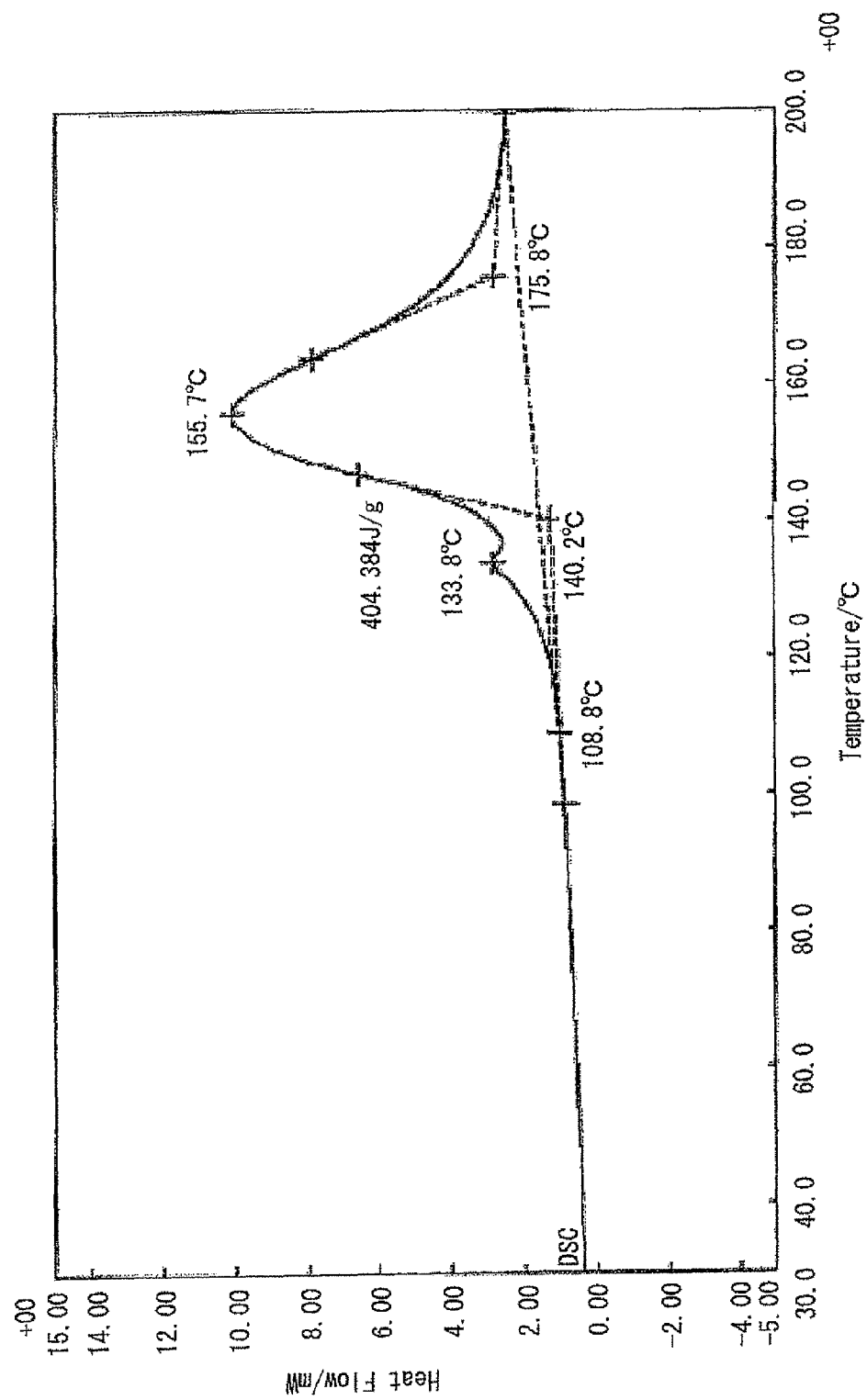
FIG. 13 is a thermal analysis (DSC) chart upon temperature variation for the clathrate according to an Example 5 and an epoxy resin.

Furthermore, a thermal analysis (DSC) chart upon temperature variation for 2-undecylimidazole and an epoxy resin is shown in FIG. 12, whereas a thermal analysis (DSC) chart upon temperature variation for the obtained clathrate and an epoxy resin is shown in FIG. 13. The curing temperature in FIG. 13 was considerably higher than the curing temperature in FIG. 12, confirming that the clathrate structure generated an improvement in the one-pot stability.

The DSC charts were prepared by mixing 4% of the imidazole with a bisphenol A epoxy resin (YD-128), and then conducting measurements.

Example 6

5 mmol (1.06 g) of 5-nitroisophthalic acid and 10 mmol (3.06 g) of 2-heptadecylimidazole were added to 30 ml of methanol, and the resulting mixture was stirred under heat and then left to stand overnight. After standing overnight, the mixture was filtered and dried under vacuum, yielding 3.16 g of a clathrate (1:2 clathrate).

Figure 14:
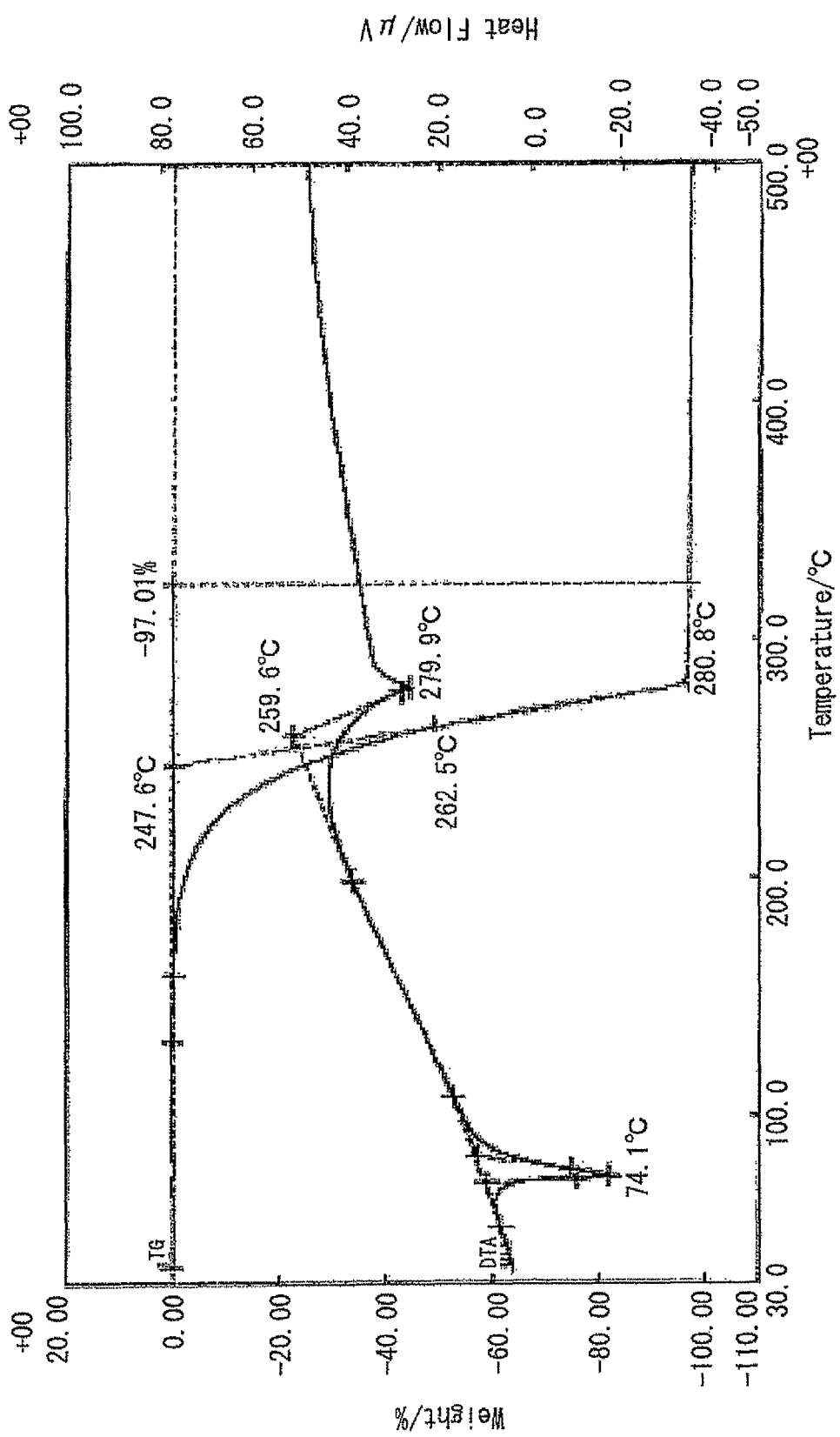
FIG. 14 is a thermal analysis (TG/DTA) chart for only 2-heptadecylimidazole.
Figure 15:
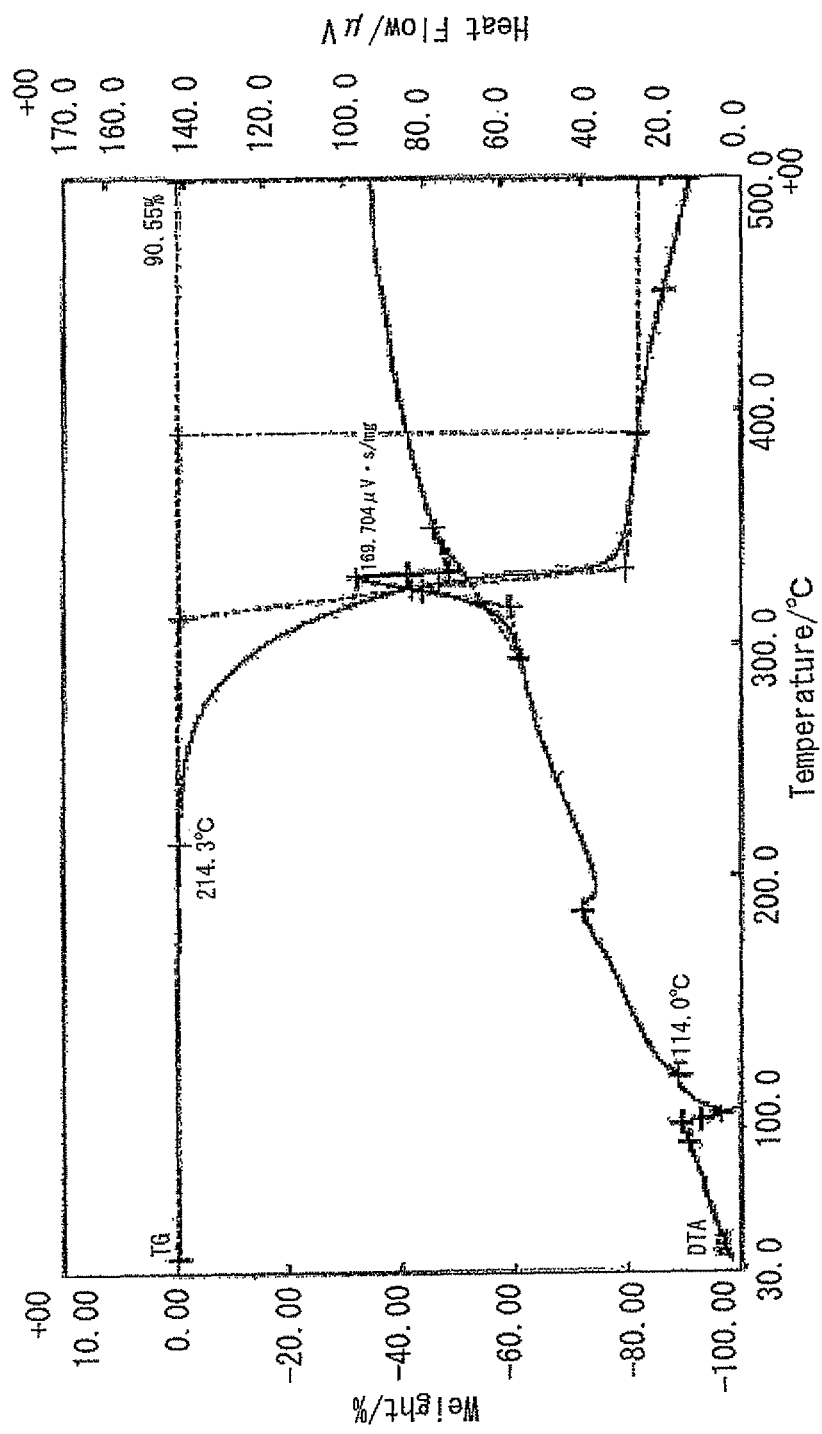
FIG. 15 is a thermal analysis (TG/DTA) chart for a clathrate according to an Example 6.

A thermal analysis (TG/DTA) chart for only 2-heptadecylimidazole is shown in FIG. 14, whereas a thermal analysis (TG/DTA) chart for the obtained clathrate crystals is shown in FIG. 15. It is thought that because the melting point for 2-undecylimidazole was not observed in the chart of FIG. 15, the obtained crystals are a clathrate compound.

Figure 16:
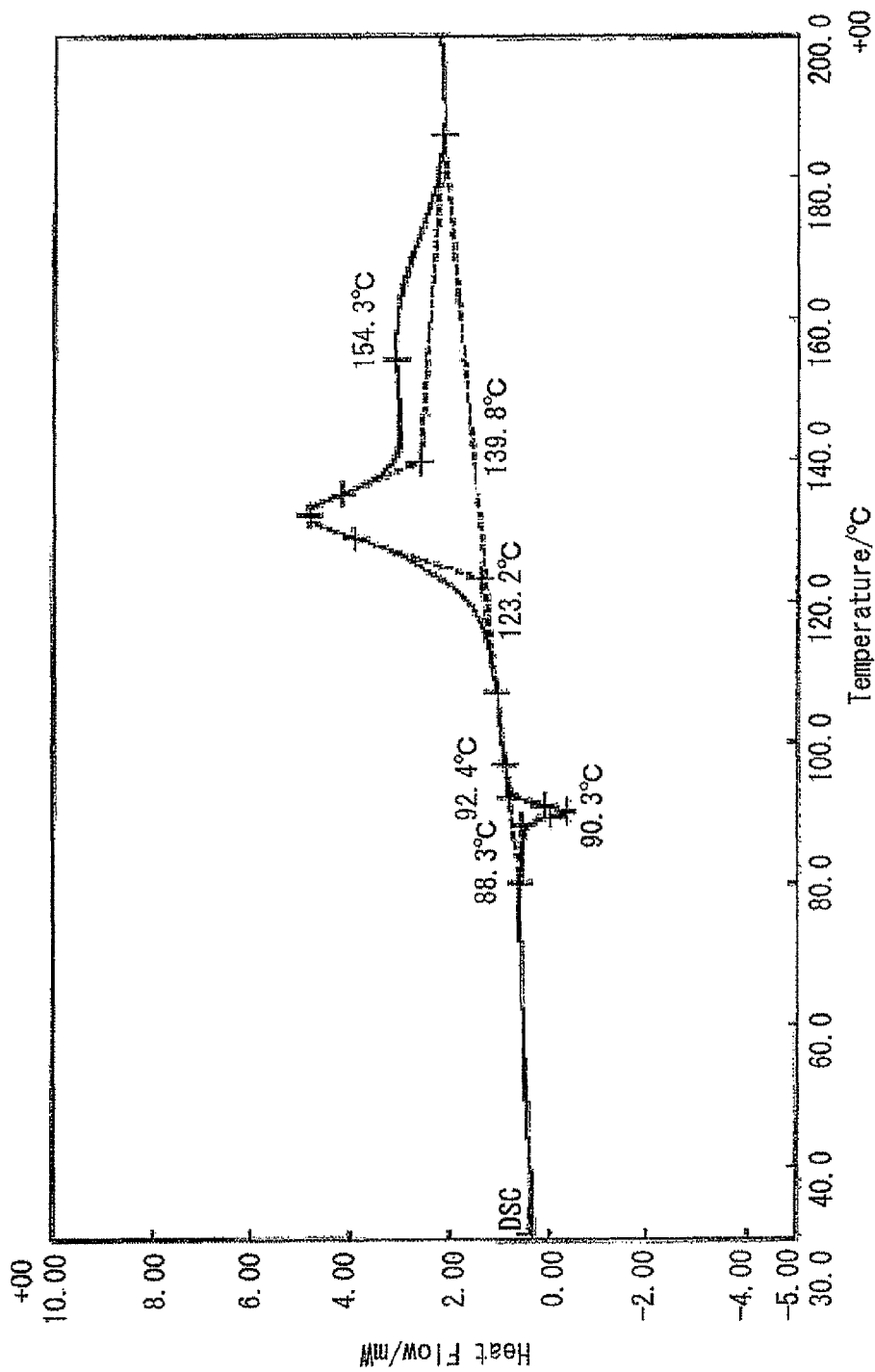
FIG. 16 is a thermal analysis (DSC) chart upon temperature variation for 2-heptadecylimidazole and an epoxy resin.
Figure 17:
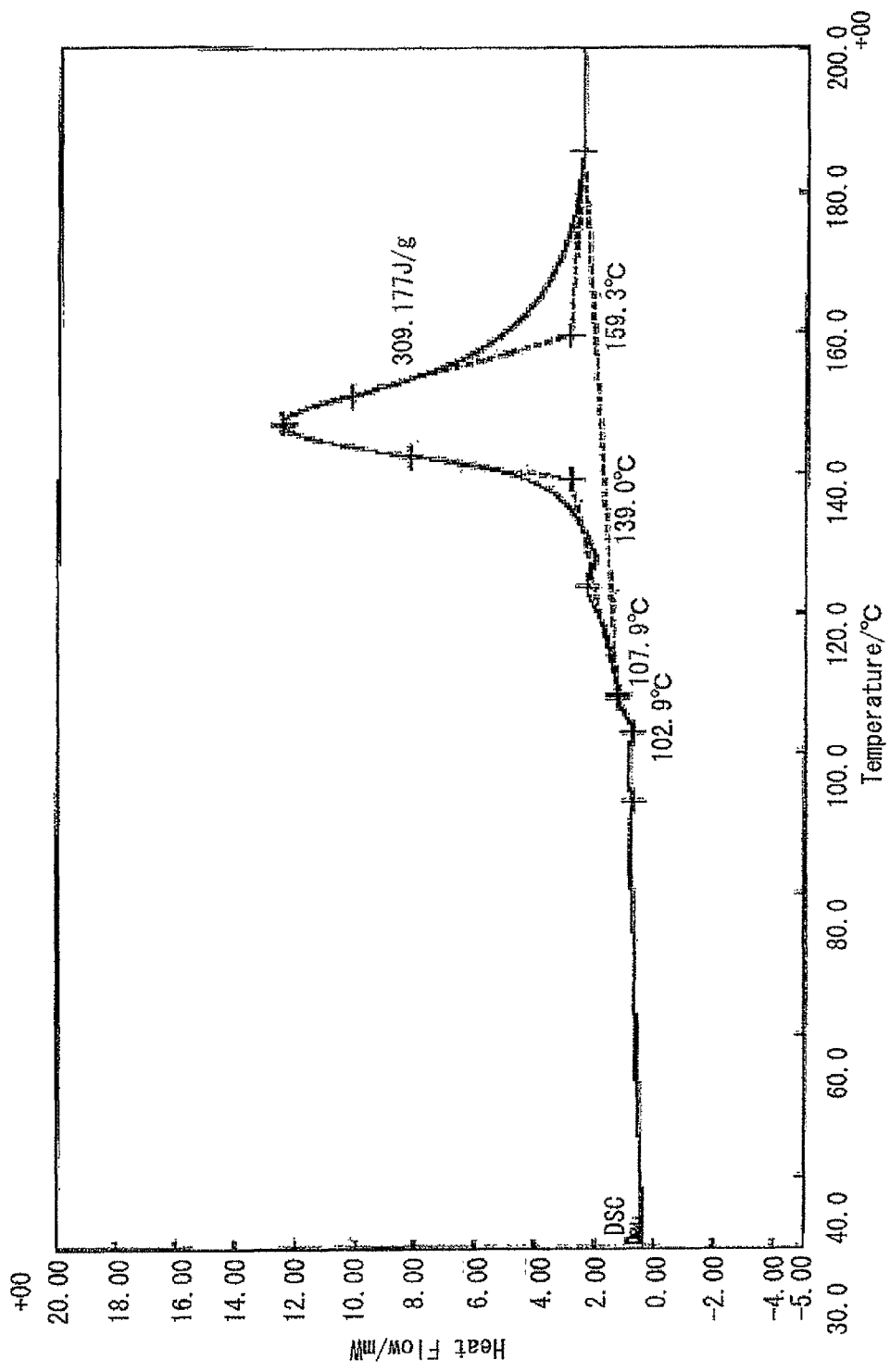
FIG. 17 is a thermal analysis (DSC) chart upon temperature variation for the clathrate according to an Example 6 and an epoxy resin.

Furthermore, a thermal analysis (DSC) chart upon temperature variation for 2-heptadecylimidazole and an epoxy resin is shown in FIG. 16, whereas a thermal analysis (DSC) chart upon temperature variation for the obtained clathrate and an epoxy resin is shown in FIG. 17. The peaks in FIG. 16 and FIG. 17 are clearly different, confirming the difference in the structure obtained as a result of the clathrate structure.

The DSC charts were prepared by mixing 4% of the imidazole with a bisphenol A epoxy resin (YD-128), and then conducting measurements.

Comparative Example 1

Using the same procedure as Example 1, a thermal analysis (DSC) chart upon temperature variation and a thermal analysis (DSC) chart at a fixed temperature (80° C.) were measured for 2-ethyl-4-methylimidazole (2E4MZ).

Comparative Example 2

A methanol solution (200 ml) containing 125 mmol (49.8 g) of 1,1,2,2-tetrakis(4-hydroxyphenyl)ethane (TEP) was heated under reflux, and a methanol solution (20 ml) containing 267 mmol (29.4 g) of 2-ethyl-4-methylimidazole was then added dropwise to the refluxed solution. After stirring for one hour, the heating was stopped, and the mixture was left to stand overnight. Subsequently, the resulting mixture was filtered and dried under vacuum, yielding 54.6 g of a clathrate (TEP-2E4MZ). Using the same procedure as Example 1, a thermal analysis (DSC) chart upon temperature variation and a thermal analysis (DSC) chart at a fixed temperature (80° C.) were measured for the thus obtained clathrate.

Comparative Example 3

15 mmol (2.5 g) of isophthalic acid and 16.5 mmol (1.8 g) of 2-ethyl-4-methylimidazole were dissolved in 15 ml of methanol under heating, and the resulting mixture was left to stand overnight. The precipitated crystals were then filtered and dried under vacuum, yielding 1.8 g of a clathrate (isophthalic acid-2E4MZ). Using the same procedure as Example 1, a thermal analysis (DSC) chart upon temperature variation and a thermal analysis (DSC) chart at a fixed temperature (80° C.) were measured for the thus obtained clathrate.

Comparative Example 4

5 mmol (0.8 g) of terephthalic acid and 10 mmol (1.1 g) of 2-ethyl-4-methylimidazole were dissolved in 15 ml of methanol under heating, and the resulting mixture was left to stand overnight. The precipitated crystals were then filtered and dried under vacuum, yielding a clathrate (terephthalic acid-2E4MZ). Using the same procedure as Example 1, a thermal analysis (DSC) chart upon temperature variation and a thermal analysis (DSC) chart at a fixed temperature (80° C.) were measured for the thus obtained clathrate.

Comparative Example 5

Using the same procedure as Example 1, a thermal analysis (DSC) chart upon temperature variation and a thermal analysis (DSC) chart at a fixed temperature (80° C.) were measured for 2-methylimidazole (2MZ).

Comparative Example 6

75.0 g of 1,1,2,2-tetrakis(4-hydroxyphenyl)ethane (TEP), 31.0 g of 2-methylimidazole and 300 ml of ethyl acetate were mixed together, and the resulting mixture was heated under reflux for 3 hours. Subsequently, the mixture was left to stand overnight, and the resulting precipitate was then filtered and dried under vacuum, yielding 95 g of a clathrate (TEP-2MZ).

Using the same procedure as Example 1, a thermal analysis (DSC) chart upon temperature variation and a thermal analysis (DSC) chart at a fixed temperature (80° C.) were measured for the thus obtained clathrate.

Comparative Example 7

10 mmol (1.5 g) of 3,5-dihydroxybenzoic acid and 10 mmol (0.8 g) of 2-methylimidazole were dissolved in 50 ml of methanol under heating, and the resulting mixture was left to stand overnight. The precipitated crystals were then filtered and dried under vacuum, yielding a clathrate (3,5-dihydroxybenzoic acid-2MZ). Using the same procedure as Example 1, a thermal analysis (DSC) chart upon temperature variation and a thermal analysis (DSC) chart at a fixed temperature (80° C.) were measured for the thus obtained clathrate.

Comparative Example 8

15 mmol (2.5 g) of isophthalic acid and 16.5 mmol (1.4 g) of 2-methylimidazole were added to 20 ml of methanol, and the resulting mixture was stirred under heat and then left to stand overnight. The resulting precipitate was then filtered and dried under vacuum, yielding 2.8 g of a clathrate (isophthalic acid-2MZ). Using the same procedure as Example 1, a thermal analysis (DSC) chart upon temperature variation and a thermal analysis (DSC) chart at a fixed temperature (80° C.) were measured for the thus obtained clathrate.

FIG. 20 shows, in graphic form, the values for the reaction start temperature, the peak top, and the reaction end temperature read from the charts shown in FIG. 2 (Example 1), FIG. 5 (Example 2) and FIG. 8 (Example 4), as well as the same values for the Comparative Examples 1-8 also shown in graphic form.

From the figures, it is evident that the clathrates according to the examples exhibit a higher reaction start temperature, which indicates an improvement in the one-pot stability. Furthermore, the clathrates according to the examples also have a small temperature difference between the reaction start temperature and the peak top, and it is thought that this indicates a higher degree of reactivity for the epoxy rings.

Figure 21:
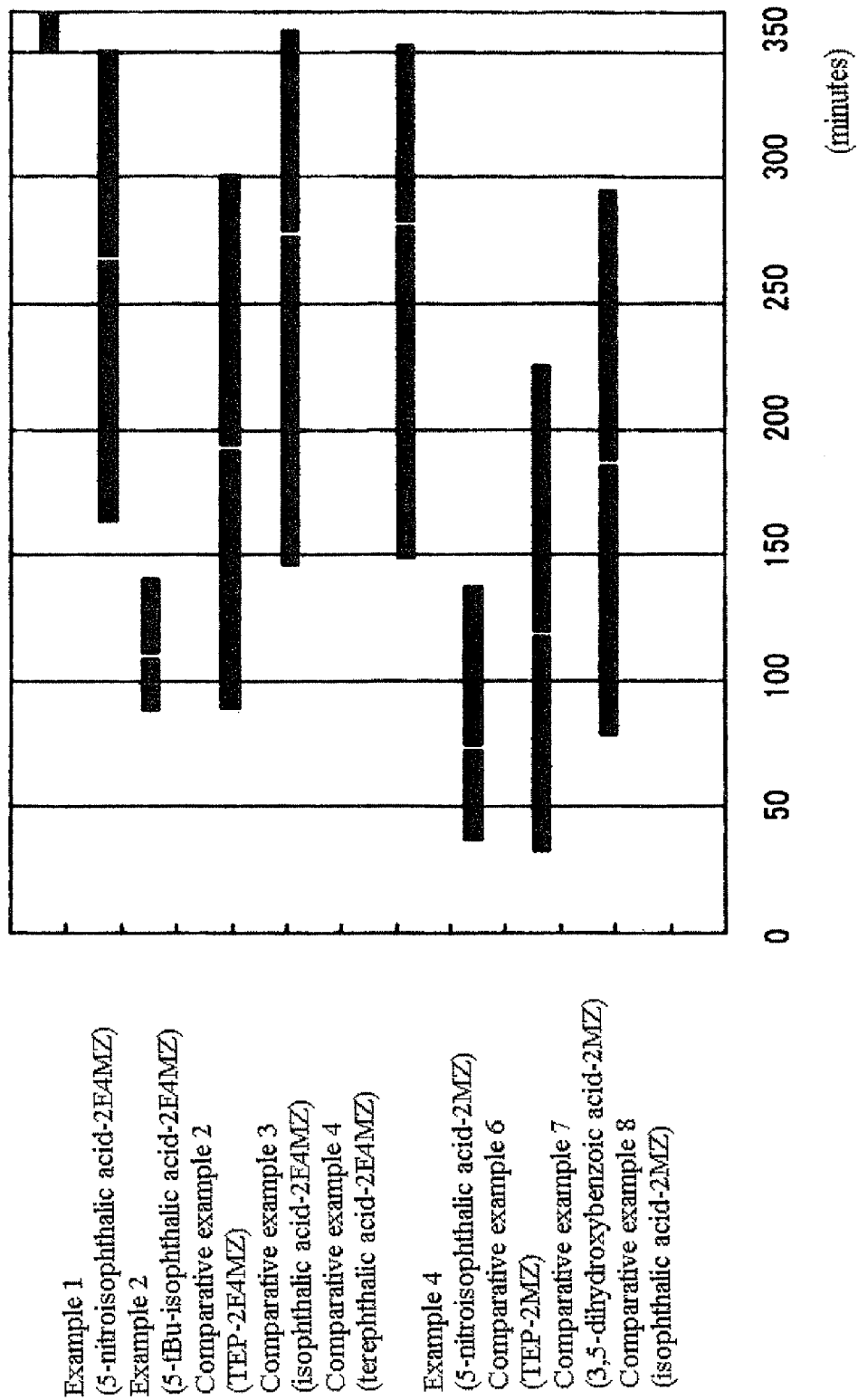
FIG. 21 is a chart showing, in graphic form, the values for the reaction start temperature, the peak top, and the reaction end temperature read from the charts shown in FIG. 3 (Example 1), FIG. 6 (Example 2) and FIG. 9 (Example 4), as well as the same values for Comparative Examples 1-8 also shown in graphic form.

FIG. 21 shows, in graphic form, the values for the reaction start temperature, the peak top, and the reaction end temperature read from the charts shown in FIG. 3 (Example 1), FIG. 6 (Example 2) and FIG. 9 (Example 4), as well as the same values for Comparative Examples 1-8 also shown in graphic form.

The fixed temperature of 80° C. is a typical temperature used during mixing of an epoxy resin and a clathrate, and therefore suppressing reaction at this temperature is extremely important. From the figures, it is evident that the clathrates according to the examples exhibit much longer time before the reaction starts and before the reaction peak, indicating an extremely favorable level of one-pot stability.

Example 7

100 mmol of 5-hydroxyisophthalic acid and 100 mmol of 2-undecylimidazole were added to 50 ml of methanol, and the resulting mixture was stirred under heated reflux in a round-bottom flask, thereby dissolving the crystals. Subsequently, the solution was left to stand at room temperature, and the crystals that precipitated from the solution were filtered and dried in a vacuum, yielding a clathrate compound (yield: 58%).

Comparative Example 9

200 mmol of isophthalic acid and 200 mmol of 2-undecylimidazole were added to 1000 ml of ethyl acetate, and the resulting mixture was stirred under heated reflux in a round-bottom flask, thereby dissolving the crystals. Subsequently, the solution was left to stand at room temperature, and the crystals that precipitated from the solution were filtered and dried in a vacuum, yielding a compound (yield: 88%).

Example 8

180 ml of an ethyl acetate solution containing 100 mmol of 2E4MZ was added to 70 ml of an ethyl acetate solution containing 100 mmol of 5-hydroxyisophthalic acid under conditions of heated reflux with stirring. Heating is subsequently stopped, and then the mixture was left to stand overnight at room temperature. The resultant was filtered and then dried in a vacuum, yielding a clathrate compound (yield: 93%).

Values for the reaction start temperature, the peak top, and the reaction end temperature were read from thermal analysis (DSC) charts upon temperature variation for the obtained compounds. The results are shown in FIG. 22.

Figure 22:
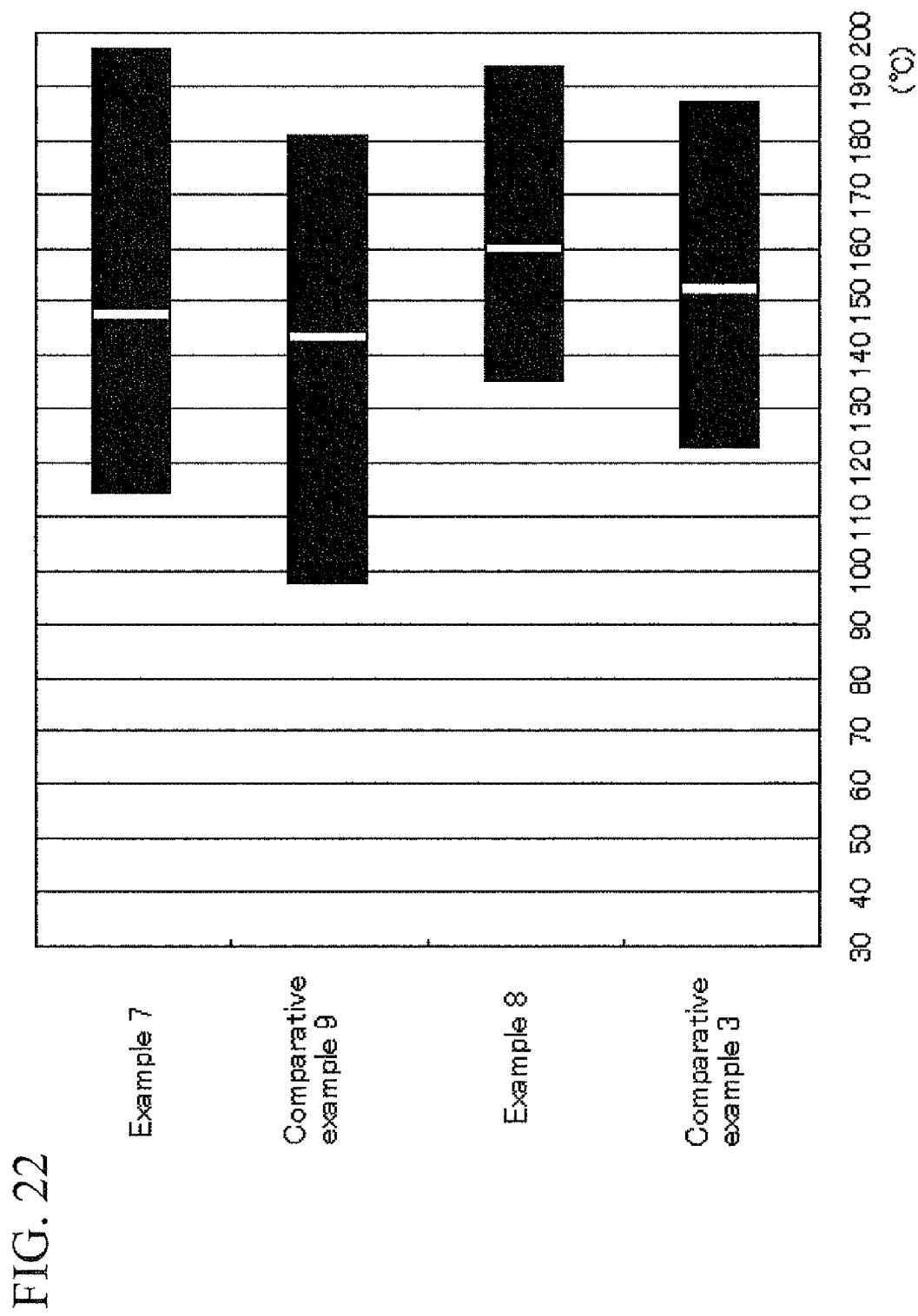
FIG. 22 is a chart showing, in graphic form, the values for the reaction start temperature, the peak top, and the reaction end temperature read from thermal analysis (DSC) charts upon temperature variation for the compounds obtained in Examples 7 and 8 and Comparative Examples 9 and 3.

As shown in FIG. 22, the compounds of Examples 7 and 8 exhibited higher reaction start temperatures than those of Comparative Examples 9 and 3, respectively. Furthermore, the clathrate compounds of Examples 7 and 8 also had smaller temperature differences between the reaction start temperature and the peak top than those of Comparative Examples 9 and 3, respectively.

The invention claimed is:

1. A clathrate compound comprising:
    an isophthalic acid compound represented by formula (I):

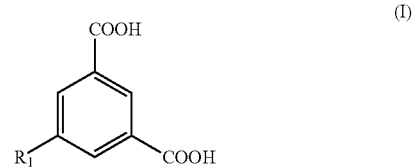

where $R_1$ represents a C1 to C6 alkyl group, a C1 to C6 alkoxy group, a nitro group, or a hydroxyl group; and
    an imidazole compound represented by formula (II):

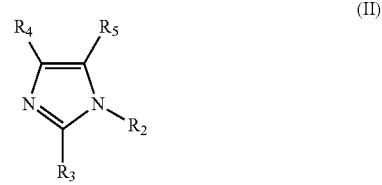

where:
    $R_2$ represents a hydrogen atom, a C1 to C10 alkyl group, a phenyl group, a benzyl group, or a cyanoethyl group, and
    $R_3$ to $R_5$ each independently represents:
        a hydrogen atom, a nitro group, or a halogen atom, or
        a C1 to C20 alkyl group that may have a substituent, a phenyl group that may have a substituent, a benzyl group that may have a substituent, or a C1 to C20 acyl group that may have a substituent.

2. The clathrate compound according to claim 1, wherein the isophthalic acid compound represented by formula (I) is 5-t-butylisophthalic acid, 5-hydroxyisophthalic acid, or 5-nitroisophthalic acid.

3. The clathrate compound according to claim 1, wherein the imidazole compound represented by formula (II) is imidazole, 2-ethyl-4-methylimidazole, 2-methylimidazole, 2-n-butylimidazole, 1-benzyl-2-methylimidazole, 2-heptadecylimidazole, 2-undecylimidazole or 2-phenyl-4-methyl-5-hydroxymethylimidazole.

4. The clathrate compound according to claim 1, wherein $R_2$ is a hydrogen atom.

5. The clathrate compound according to claim 1, wherein the compound is in a powdered form.

6. A curing catalyst for an epoxy resin, comprising a clathrate compound according to claim 1.

7. A curing catalyst for an epoxy resin, comprising a clathrate compound according to claim 2.

8. A curing catalyst for an epoxy resin, comprising a clathrate compound according to claim 3.

9. A curing catalyst for an epoxy resin, comprising a clathrate compound according to claim 4.

10. A curing catalyst for an epoxy resin, comprising a clathrate compound according to claim 5.

11. A method for producing a clathrate compound, comprising:

dissolving or suspending in a solvent at least an isophthalic acid compound represented by formula (I):

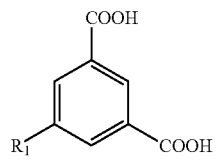

(I)

where $R_1$ represents a C1 to C6 alkyl group, a C1 to C6 alkoxy group, a nitro group, or a hydroxyl group, and an imidazole compound represented by formula (II):

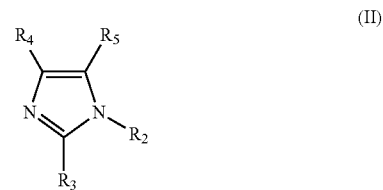

(II)

where:

$R_2$ represents a hydrogen atom, a C1 to C10 alkyl group, a phenyl group, a benzyl group, or a cyanoethyl group, and $R_3$ to $R_5$ each independently represents:

a hydrogen atom, a nitro group, or a halogen atom, or a C1 to C20 alkyl group, a phenyl group that may have a substituent, a benzyl group that may have a substituent, or a C1 to C20 acyl group that may have a substituent; and subsequently conducting heating.

12. The method according to claim 11, further comprising performing a crystallization after heating.

* * * * *